United States Patent
Kappeler et al.

(10) Patent No.: US 7,270,989 B2
(45) Date of Patent: Sep. 18, 2007

(54) METHOD OF PRODUCING NON-BOVINE CHYMOSIN AND USE HEREOF

(75) Inventors: Stefan Kappeler, Baden (CH); Zakaria Farah, Thalwil (CH); Johannes Maarten van den Brink, Herlev (DK); Henrik Rahbek-Nielsen, Birkerød (DK); Peter Budtz, Frederiksberg (DK)

(73) Assignees: CHR. Hansen A/S, Horsholm (DK); Eidgenossische Technische Hochschule Zurich, Zurich (CH)

( * ) Notice: Subject to any disclaimer, the term of this patent is extended or adjusted under 35 U.S.C. 154(b) by 391 days.

(21) Appl. No.: 10/807,115

(22) Filed: Mar. 24, 2004

(65) Prior Publication Data

US 2004/0180410 A1    Sep. 16, 2004

Related U.S. Application Data

(63) Continuation of application No. 09/985,936, filed on Nov. 6, 2001, now abandoned, which is a continuation-in-part of application No. 09/705,917, filed on Nov. 6, 2000, now abandoned.

(51) Int. Cl.
| | |
|---|---|
| C12N 9/64 | (2006.01) |
| C12N 1/15 | (2006.01) |
| C12N 1/21 | (2006.01) |
| C12N 5/04 | (2006.01) |
| C12N 5/06 | (2006.01) |
| C12N 15/63 | (2006.01) |
| C07H 21/04 | (2006.01) |

(52) U.S. Cl. ............... 435/226; 435/69.7; 435/252.3; 435/254.11; 435/320.1; 435/325; 435/348; 435/410; 536/23.2; 536/23.4

(58) Field of Classification Search ............ None
See application file for complete search history.

(56) References Cited

U.S. PATENT DOCUMENTS 5,364,770 A    11/1994   Berka et al.

FOREIGN PATENT DOCUMENTS

| EP | 0121775 | 10/1984 |
| WO | 9416086 | 7/1994 |
| WO | 9529999 | 11/1995 |
| WO | 9636718 | 11/1996 |
| WO | 0158924 | 8/2001 |

OTHER PUBLICATIONS

Kappeler et al. (2006) Biochem. Biophys. Res. Comm., vol. 342, No. 2, pp. 647-654.*
Francky, et al., *A basic residue at position 36p of the propeptide is not essential for the correct folding and subsequent autocatalytic activation of prochymosin*, Eur. J. Biochem., vol. 268, pp. 2362-2368, Apr. 2001.
Dunn-Coleman, et al., "Commercial Levels of Chymosin Production by *Aspergillus*," *Bio/Technology* 9:976-981 (Oct. 1991).
Elagamy, "Physicochemical, molecular and immunological characterization of camel calf rennet: a comparison with buffalo rennet," *Journal of Dairy Research* 67:73-81 (2000).
Foltmann, et al., "The complete amino acid sequence of prochymosin," *Proc. Natl. Acad. Sci. USA* 74(6):2321-2324 (Jun. 1977).
Houen, et al., "The Primary Structure and Enzymic Properties of Porcine Prochymosin and Chymosin," *Int. J. Biochem. Cell Biol.* 28(6):667-675 (1996).
Kappeler, S., "Compositional and Structural Analysis of Camel Milk Proteins with Emphasis on Protective Proteins," Dissertation ETH No. 12947, Swiss Federal Institute of Technology, (1998).
Wangoh, et al., "Extraction of camel rennet and its comparison with calf rennet extract," Milchwissenschaft 48:322-325 (1993).
Ward, et al., "Improved production of chymosin in *Aspergillus* by expression as a glycoamylase-chymosin fusion," *Bio/Technology* 8:435-440 (May 1990).
Ward, et al., "Use of *Aspergillus* overproducing mutants, cured for integrated plasmid, to overproduce heterologous proteins," *Applied Microbiol. Biotechnol.* 39:738-743 (1993).
Bork , Genome Research, 10:398-400, 2000.
Broun et al. , Science 282:1315-1317, 1998.
Van de Loo et al. , Proc. Natl. Acad. Sci. 92:6743-6747, 1995.
Seffernick et al. , J. Bacteriol. 183(8):2405-2410, 2001.
Witkowski et al. , Biochemistry 38:11643-11650, 1999.
Nomura et al. , Appl. Microbiol. Biotechnol. 42:865-870, 1995.
Pungercar et al. , Nucleic Acids Research 18(15):4602, 1990.

* cited by examiner

*Primary Examiner*—Elizabeth Slobodyansky
(74) *Attorney, Agent, or Firm*—Iver P. Cooper

(57) ABSTRACT

A method of recombinantly producing a non-bovine preprochymosin, prochymosin or chymosin derived from ruminant species including deer species, buffalo species, antelope species, giraffe species, ovine species and caprine species; Camelidae species such as *Camelus dromedarius*; porcine species; or Equidae species. The recombinant enzymes are used in milk coagulating compositions in cheese manufacturing based on cow's milk and milk from any animal species which are used in cheese manufacturing including camel's milk.

19 Claims, 10 Drawing Sheets

METHOD OF PRODUCING NON-BOVINE CHYMOSIN AND USE HEREOF

This is a continuation of Ser. No. 09/985,936 filed Nov. 6, 2001, now abandoned; which is a continuation-in-part of 09/705,917 filed Nov. 6, 2000, now abandoned.

The prior application(s) set forth above are hereby incorporated by reference in their entirety.

FIELD OF INVENTION

The present invention relates generally to the field of cheese manufacturing. In particular, novel recombinant means of providing milk-clotting enzymes of non-bovine, ie non-*Bos taurus*, animal origin are provided. Specifically, the invention pertains to a process of recombinantly providing pre-prochymosin, prochymosin and chymosin of non-bovine origin including such enzymes that are derived from camels.

TECHNICAL BACKGROUND AND PRIOR ART

Enzymatic coagulation of milk-by-milk clotting enzymes, such as chymosin and pepsin, is one of the most important processes in the manufacture of cheeses. Enzymatic milk coagulation is a two-phase process: a first phase where a proteolytic enzyme, chymosin or pepsin, attacks κ-casein, resulting in a metastable state of the casein micelle structure and a second phase, where the milk subsequently coagulates and forms a coagulum.

Chymosin (EC 3.4.23.4) and pepsin (EC 3.4.23.1), the milk clotting enzymes of the mammalian stomach, are aspartic proteases belonging to a broad class of peptidases (Kappeler, 1998). Aspartic proteases are found in eukaryotes, retroviruses and some plant viruses. Eukaryotic aspartic proteases are monomers of about 35 kDa, which are folded into a pair of tandemly arranged domains with a high degree of similarity, i.e. 20% or higher. The overall secondary structure consists almost entirely of pleated sheets and is low in α-helices. Each domain contains an active site centred on a catalytic aspartyl residue with a consensus sequence hydrophobic-Asp-Thr-Gly-Ser/Thr (SEQ ID NO:7) which aids in maintaining the correct Φ-loop conformation of the site, and with multiple hydrophobic residues near the aspartic residue. The two catalytic sites are arranged face-to-face in the tertiary structure of correctly folded proteins. In bovine chymosin, the distance between the aspartic side chains is about 3.5 Å. The residues are reported to be extensively hydrogen bonded, concomitantly with the adjacent threonine residues, to the corresponding residues of the other domain or the neighbouring atoms of the own domain, to stabilise the correct position. Optimum activity of an aspartic protease is achieved when one of the aspartic residues is protonated and the other one is negatively charged. The active sites of chymosin and other aspartic proteases are embedded, with low accessibility, in the middle of a cleft, about 40 Å in length, which separates the two domains, and which is covered by a flap that, in bovine and camel chymosin, extends from about Leu73 to Ile85 in the N-terminal domain.

When produced in the gastric mucosal cells, chymosin and pepsin occur as enzymatically inactive pre-prochymosin and pre-pepsinogen, respectively. When chymosin is excreted, an N-terminal peptide fragment, the pre-fragment (signal peptide) is cleaved off to give prochymosin including a pro-fragment. Prochymosin is a substantially inactive form of the enzyme which, however, becomes activated under acidic conditions to the active chymosin by autocatalytic removal of the pro-fragment. This activation occurs in vivo in the gastric lumen under appropriate pH conditions or in vitro under acidic conditions.

The structural and functional characteristics of bovine, ie *Bos taurus*, pre-prochymosin, prochymosin and chymosin have been studied extensively (Foltman et al. 1977). The pre-part of the bovine pre-prochymosin molecule comprises 16 aa residues and the pro-part of the corresponding prochymosin has a length of 42 aa residues. Foltman et al., 1997 have shown that the active bovine chymosin comprising 323 aa is a mixture of two forms, A and B, both of which are active, and sequencing data indicate that the only difference between those two forms is an aspartate residue at position 290 in chymosin A and a glycine residue at that position in chymosin B.

Whereas chymosin is produced naturally in mammalian species including ruminant species such as bovines, caprines, buffaloes and ovines; pigs (Houen et al., 1996); Camelidae species; primates including humans and monkeys; and rats, bovine chymosin and (to a lesser extent) caprine chymosin are presently the only of these animal chymosin species that are commercially available to the dairy industry. Bovine chymosin, in particular calf chymosin, is commercially available both as stomach enzyme extracts (rennets) comprising the natively produced chymosin and as recombinantly produced chymosin which is expressed in bacterial, yeast or fungal host cells (see e.g. WO 95/29999, Ward et al. 1990).

Recently, studies on functional characteristics of rennet extracted from the stomach of *Camelus dromedarius* chymosin have been reported (Wangoh et al., 1993; Elagamy, 2000) and it has been found that the clotting time of camel's milk is significantly reduced when camel rennet is used instead of bovine calf rennet. Fractions of crude camel and calf rennets, which were isolated by anion-exchange chromatography, have been tested for their respective capabilities to clot camel's milk and cow's milk and it was found that the main clotting activity of calf rennet (i.e. an extract containing both chymosin and pepsin) resides in the pepsin fraction, i.e. bovine chymosin is substantially inactive in respect of clotting camel's milk, whereas the main clotting activity of camel rennet extracts on camel's milk resided in a first fraction that, compared to calf chymosin, eluted at a somewhat lower NaCl concentration. The active enzyme of this fraction has not yet been characterised, but it is assumingly chymosin. It has also been demonstrated that this camel rennet fraction has a clotting activity on cow's milk that is similar to that of bovine chymosin (Wangoh et al., 1993). It is evident, therefore, that more effective clotting of camel's milk could be achieved at an industrial level were camel chymosin commercially available and it is also conceivable that camel chymosin is highly suitable as a cow's milk clotting enzyme as well.

The primary structure of chymosin isolated from gastric mucosa of camels has been determined (Kappeler, 1998). The mature and active form of camel chymosin is 323 aa residues long and it has a molecular weight of 35.6 kDa and an isoelectric point at pH 4.71. It shows 85.1% aa sequence identity with bovine chymosin.

Presently, bovine chymosin is manufactured industrially using recombinant DNA technology, e.g. using filamentous fungi such as *Aspergillus* species (see e.g. Ward, 1990), yeast strains, e.g. of *Klyuveromyces* species, or bacterial species, e.g. *E. coli*, as host organisms. Such recombinant microbial production strains are constructed and continuously improved using DNA technology as well as classical strain improvement measures directed towards optimising the expression and secretion of the heterologous protein, but it is evident that the productivity in terms of overall yield of gene product is an important factor for the cost effectiveness of industrial production of the enzyme. Accordingly, a continued industrial need exists to improve the yield of chymosin in recombinant expression systems.

Whereas efforts to improve yields of chymosin activity up till now have exclusively been concerned with chymosin of bovine origin, the industry has not yet explored the possibility of providing effective chymosin preparations based on non-bovine, ie non-*Bos taurus*, chymosin species. However, the present inventors have surprisingly found that it is possible to provide industrially highly useful non-bovine chymosin using recombinant DNA technology at a production yield level which, relative to that which can be obtained in current, optimised bovine chymosin production systems, is significantly improved.

In addition to the potential of significantly improved chymosin production cost-effectiveness, the provision of such non-bovine chymosin species at a commercial level makes available chymosin products that are not only capable of clotting cow's milk at least as effectively as chymosin of bovine origin, but which, additionally, are capable of more effectively clotting milk from other animal species including milk of the source species. Specifically, the invention has made it possible to provide, for the first time, camel chymosin in sufficient quantities to render an industrial, cost-effective and high quality production of cheese based on camel's milk possible, which, due to the scarcity of camel calf stomach material, has not hitherto been possible.

Additionally, it has been discovered that camel chymosin has a high clotting activity on cow's milk, which renders the enzyme useful for manufacturing cheese based on cow's milk. It was a surprising finding of the present inventors that camel chymosin has a specific κ-casein hydrolysing activity (Phe-Met 105/106), i.e. C/P ratio as defined hereinbelow, which is superior to that of bovine chymosin. A higher C/P ratio implies generally that the loss of protein during cheese manufacturing due to non-specific protein degradation is reduced, i.e. the yield of cheese is improved, and that the development of bitter taste in the cheese during maturation is reduced.

SUMMARY OF THE INVENTION

The invention relates in one aspect to a method of producing a non-bovine pre-prochymosin, prochymosin or chymosin, the method comprising the steps of (i) isolating or constructing a nucleic acid sequence coding for the pre-prochymosin, prochymosin or chymosin, (ii) constructing an expression vector comprising said coding sequence and, operably linked thereto, appropriate expression signals permitting the pre-prochymosin, prochymosin or chymosin to be expressed in a host cell, (iii) transforming said host cell with the expression vector, (iv) cultivating the thus transformed host cell under conditions where the coding sequence is expressed and (v) harvesting the pre-prochymosin, prochymosin or chymosin. As used herein the expression "non-bovine pre-prochymosin, prochymosin or chymosin" refers to such enzymes or precursors herefor that are derived from a mammalian species other than *Bos taurus*.

In further aspects, the invention pertains to a DNA construct capable of expressing non-bovine pre-prochymosin, prochymosin or chymosin, said construct comprising an expression vector comprising a nucleic acid sequence comprising a gene coding for the pre-prochymosin, prochymosin or chymosin and, operably linked thereto, appropriate expression signals permitting the pre-prochymosin, prochymosin or chymosin to be expressed in a host cell, and to a host cell transformed with such a DNA construct.

In still further aspects a composition is provided comprising a non-bovine pre-prochymosin, prochymosin or chymosin produced by the above method including such an enzyme that is in a substantially deglycosylated form and a method of manufacturing cheese, comprising adding a milk clotting effective amount of such a composition to milk and carrying out appropriate further cheese manufacturing steps.

In yet another aspect, the invention relates to a method of manufacturing cheese, comprising adding a milk clotting effective amount of a non-bovine prochymosin or chymosin to the milk and carrying out appropriate further cheese manufacturing steps, the non-bovine prochymosin or chymosin having in said milk a C/P ratio as determined herein which is in the range of 2-20.

In other aspects the invention provides a milk clotting composition comprising a bovine milk clotting enzyme selected from prochymosin, chymosin and pepsin and a non-bovine milk clotting enzyme selected from prochymosin, chymosin, pepsin and a microbial aspartic protease and a method of manufacturing cheese from milk, comprising adding to milk a milk clotting effective amount of such a composition, and carrying out appropriate further cheese manufacturing steps.

DETAILED DISCLOSURE OF THE INVENTION

In accordance with the invention, there is, in one aspect of the invention, provided a method of recombinantly producing pre-prochymosin, prochymosin or chymosin of non-bovine origin.

For the purposes of this application, the expression "non-bovine origin" refers to any non-*Bos taurus* mammalian species where pre-prochymosin is produced naturally in the gastrointestinal tract. Such species include any of those mentioned above, e.g. ovine species, caprine species and Camelidae species comprising the genus *Camelus* with the two species *Camelus dromedarius* and *Camelus bactrianus*; buffalo species including water buffaloes, Indian buffaloes and Cape buffaloes, the genus *Lama* including *Lama glama*, *Lama guanicoe* and *Lama paco*; and the genus *Vicugna*. Camels are ruminating, but do not belong to the suborder Ruminantia as do e.g. bovine, ovine and caprine species, but they belong to the suborder Tylopoda.

However, a non-bovine chymosin as used in this context may also include a chymosin molecule encoded by a cluster or a shuffling of DNA segments of different origin resulting in complex rearrangements of the DNA. Shuffling of DNA segments or gene shuffling is in the present invention in general to be construed as a method for the construction of chimeric genes resulting in genes coding for chimeric proteins. Such proteins will consist of domains derived from two or more parental proteins. The chimeric genes may be constructed either on the basis of rational design based on knowledge of protein function or on the basis of combinatorial laboratory methods generating random chimeric genes. Such random combinatorial libraries can be screened for the identification of optimal enzymes by a variety of screening procedures.

Prochymosin is in the present context to be understood as the precurser or proenzyme of chymosin. Prochymosin appears to possess a basic leader sequence (pro-part) on the N-terminal side of chymosin and said leader sequence is believed to be cleaved off during activation of the prochymosin. Furthermore in this context preprochymosin consists of prochymosin to which is added on the N-terminal end of prochymosin a hydrophobic leader sequence. This leader sequence, also called secretion signal or prepart, is cleaved off when the protein is secreted. Chymosin is in the cell initially synthesised as pre-prochymosin. (Harris, T. J., Lowe, P. A., Lyons, A., Thomas, P. G., Millican, T. A., Ptael, T. P., Bose, C. C., Carey, N. H., Doel, M. T. Nucleic acid Research 1982, Apr. 10, 2177-2187 Molecular cloning and nucleotide sequence of cDNA coding for calf preprochymosin.)

In an initial step of this method, a nucleic acid sequence, i.e. a polynucleotide, of non-bovine origin that codes for pre-prochymosin, prochymosin or chymosin is provided. The skilled artisan will appreciate that several approaches for obtaining such a sequence can be used including one based on the isolation of mRNA from mucosal cells of the selected source animal species and using this RNA as template in a nucleotide amplification procedure such as a PCR reaction using suitable sense and anti-sense primers which e.g. may be constructed synthetically based on the known sequences for bovine chymosin species. The person of skill in the art will appreciate that other methods for obtaining a coding sequence according to the invention may be used such as hybridisation procedures using as probes fragments of known coding sequences for chymosin that will permit the presence of homologous DNA or RNA to be detected in preparations of cells of the selected non-bovine source species. Alternatively, it is possible to construct a coding sequence based on the isolation of the non-bovine pre-prochymosin, prochymosin or chymosin followed by determining the amino acid sequence of the enzyme or fragments hereof which in turn permits the construction of primer oligonucleotides for detection and construction of coding sequences. The basic techniques that are required in the above procedures of obtaining coding sequences are generally within the common knowledge of the skilled artisan (Sambrook et al., 1989).

Having isolated or constructed the nucleotide sequence coding for the non-bovine pre-prochymosin, prochymosin or chymosin an expression vector is constructed that comprises the coding sequence and, operably linked thereto, appropriate expression signals, i.e. sequences to control or regulate the expression, permitting the pre-prochymosin, prochymosin or chymosin to be expressed in a selected host cell. An expression vector usually includes the components of a typical cloning vector, i.e. an element that permits autonomous replication of the vector in the selected host organism and one or more phenotypic markers for selection purposes. A suitable expression vector may further comprise one or more expression signals such as promoter sequences, operators, ribosome binding sites, translation initiation sites and/or sequences coding for repressor or activator substances. To permit the secretion of the expressed polypeptide, a signal sequence may be inserted upstream of the coding sequence for the pre-prochymosin, prochymosin or chymosin. In the present context, the term "expression signal" includes any of the above control sequences, repressor or activator substances and signal sequences. For expression under the direction of control sequences, the coding sequence is operably linked to the control sequences in proper manner with respect to expression.

In accordance with the invention, an expression vector carrying the nucleotide sequence coding for pre-prochymosin, prochymosin or chymosin can be any vector that is capable of expressing the coding sequence in the selected host organism, and the choice of vector type will depend on the host cell into which it is to be introduced. Thus, the vector may be an autonomously replicating vector, i.e. a vector that exists as an extrachromosomal entity, the replication of which is independent of chromosomal replication in the host cells, e.g. a plasmid, a bacteriophage, a minichromosome or an artificial chromosome. Alternatively, the vector may be a vector which, when introduced into a host cell, is integrated into the host cell genome and replicated with the chromosome, including a transposable element.

In the vector, the nucleotide sequence coding for the non-bovine pre-prochymosin, prochymosin or chymosin is operably combined with a suitable promoter sequence. The promoter may be any DNA sequence, which confers transcriptional activity to the host organism of choice and may be derived from genes encoding proteins, which are either homologous or heterologous to the host organism. Examples of suitable promoters for directing the transcription of the coding sequence of the invention in a bacterial host include the promoter of the lac operon of *E. coli*, the tac promoter, the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus amyloliquefaciens* α-amylase gene (amyQ), the promoters of the *Bacillus subtilis* xylA and xylB genes and promoters of lactic acid bacterial origin such as the regulatable promoters disclosed in WO 94/16086, which is incorporated herein by reference.

For transcription in a fungal species, examples of useful promoters are those derived from the genes encoding the *Pichia pastoris* alcohol oxidase, *Aspergillus oryzae* TAKA amylase, *Rhizomucor miehei* aspartic proteinase, *Aspergillus niger* neutral-amylase, *Aspergillus niger* acid stable-amylase, *A. niger* glucoamylase, *A. niger* gpdA, *A. niger* pepA, *Rhizomucor miehei* lipase, *Aspergillus oryzae* alkaline protease, *Aspergillus oryzae* triose phosphate isomerase or *Aspergillus nidulans* acetamidase, *A. nidulans* gpdA and a *Trichoderma reseei* chbl promoter. As examples of suitable promoters for expression in a yeast species the Gal 1 and Gal 10 promoters of *Saccharomyces cerevisiae* can be mentioned. When expressed in a bacterial species such as *E coli*, a suitable promoter may be selected from a bacteriophage promoter including a T7 promoter or a lambda bacteriophage promoter.

The vector comprising the DNA fragment encoding the non-bovine pre-prochymosin, prochymosin or chymosin active polypeptide may also comprise a selectable marker, e.g. a gene the product of which complements a defect in the host organism such as a mutation conferring an auxotrophic phenotype, or the marker may be one which confers antibiotic resistance or resistance to heavy metal ions.

In one specific embodiment, the expression vector is derived from pGAMpR as described in Ward et al., 1990 by substituting the coding sequence of that vector for bovine prochymosin with a coding sequence for the non-bovine pre-prochymosin, prochymosin or chymosin. An example of such a pGAMpR-derived expression vector is pGAMpR-C deposited in an *Aspergillus niger* var. *awamori* host environment under the accession Nos. CBS 108915 and CBS 108916, respectively.

The person of skill in the art will readily appreciate that any sequence coding for a non-bovine pre-prochymosin, prochymosin or chymosin constructable as described above can be modified by substituting, deleting, inserting or adding one or more nucleosides to obtain a sequence coding for a non-bovine pre-prochymosin, prochymosin or chymosin comprising the amino acid sequence of the naturally produced non-bovine enzyme or having, relative to the naturally produced non-bovine enzyme, a modified amino acid sequence. Such a modified coding sequence includes a chimeric sequence comprising parts of two or more coding sequences isolated or derived from non-bovine animal species and chimeric coding sequences comprising part of a coding sequence from one or more non-*Bos taurus* species and part of a *Bos taurus* coding sequence.

In a subsequent step of the method a suitable host cell is transformed with the expression vector. The host cell may be transformed with an autonomously replicating vector or a vector that permits that the coding sequence becomes integrated into the host cell chromosome. Such an integration is generally considered to be advantageous as the coding sequence is more likely to be stably maintained in the cell. Integration of the coding sequence into the host chromosome may be carried out according to conventional methods such as e.g. by homologous or heterologous recombination or by means of a transposable element.

In accordance with the invention, the host organism may be a cell of a higher organism such as an animal cell, including a mammal, an avian or an insect cell, or a plant cell. However, in preferred embodiments, the host organism is a microbial cell, e.g. a bacterial or a fungal cell including a yeast cell.

Examples of suitable bacterial host organisms are gram positive bacterial species such as *Bacillaceae* including *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium* and *Bacillus thuringiensis, Streptomyces* species such as *Streptomyces murinus*, lactic acid bacterial species including *Lactococcus* spp. such as *Lactococcus lactis, Lactobacillus* spp. including *Lactobacillus reuteri, Leuconostoc* spp. and *Streptococcus* spp. Alternatively, strains of a gram negative bacterial species such as a species belonging to Enterobacteriaceae, including *E. coli* or to Pseudomonadaceae may be selected as the host organism.

A suitable yeast host organism may advantageously be selected from a species of *Saccharomyces* including *Saccharomyces cerevisiae* or a species belonging to *Schizosaccharomyces*. Further useful yeast host organisms include *Pichia* spp. such as methylotrophic species hereof, including *Pichia pastoris*, and *Klyuveromyces* spp. including *Klyuveromyces lactis*.

Suitable host organisms among filamentous fungi include species of *Acremonium, Aspergillus, Fusarium, Humicola, Mucor, Myceliophtora, Neurospora, Penicillium, Thielavia, Tolypocladium* or *Trichoderma*, such as e.g. *Aspergillus aculeatus, Aspergillus awamori, Aspergillus foetidus, Aspergillus japonicus, Aspergillus oryzae, Aspergillus nidulans* or *Aspergillus niger*, including *Aspergillus niger* var. *awamori, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichiodes, Fusarium sulphureum, Fusarium torulosum, Fusarium trichothecioides, Fusarium venenatum, Humicola insolens, Humicola langinosa, Mucor miehei, Myceliophtora thermophila, Neurospora crassa, Penicillium chrysogenum, Penicillium camenbertii, Penicillium purpurogenum, Rhizomucor miehei, Thielavia terestris, Trichoderma harzianum, Trichoderma koningii, Trichoderma longibrachiatum, Trichoderma reesii* or *Trochoderma viride*.

Examples of *Aspergillus niger* var. *awamori* strains transformed with a vector expressing non-bovine pre-prochymosin, prochymosin or chymosin include the strains deposited under the accession Nos. 108915 and 108916.

Some of the above useful host organisms, such as fungal species or gram positive bacterial species, may be transformed by a process which involves protoplast formation and transformation of the protoplasts followed by regeneration of the cell wall in a manner known per se.

In subsequent steps the thus transformed host cell is cultivated under conditions where the coding sequence is expressed, and the pre-prochymosin, prochymosin or chymosin is harvested. The medium used to cultivate the transformed host cells may be any conventional medium suitable for growing the host cells in question and obtaining expression of the polypeptide. Suitable media are available from commercial suppliers or can be prepared according to published recipes.

The resulting non-bovine pre-prochymosin, prochymosin or chymosin is typically recovered or harvested from the cultivation medium by conventional procedures including separating the host cells from the medium by centrifugation or filtration, if necessary, after disruption of the cells, followed by precipitating the proteinaceous components of the supernatant or filtrate e.g. by adding a salt such as ammonium sulphate, followed by a purification step. Alternatively, the cell-free cultivation medium may also, optionally after concentrating or diluting it or addition of conventional additives, be used directly as a coagulant product for cheese manufacturing.

It will be appreciated that the non-bovine pre-prochymosin, prochymosin or chymosin as isolated can be subjected to sequence modifications by deleting, substituting, modifying or adding one or more amino acids as long as the resulting modified molecule retains at least part of the milk clotting activity of the non-bovine pre-prochymosin, prochymosin or chymosin as isolated. Such modifications can readily be performed by the person of skill in the art using methods for protein modifications that are commonly known in the art.

In accordance with the invention, the nucleotide sequence coding for non-*Bos taurus* pre-prochymosin, prochymosin or chymosin is isolated or derived from a mammalian species selected from the group consisting of a ruminant species, a Camelidae species, a porcine species, an Equidae species and a primate species. A ruminant species source animal may be selected from camel species, deer species, buffalo species, antelope species, giraffe species, ovine species and caprine species. A particularly interesting source animal is *Camelus dromedarius*.

It has been found that expression and secretion of a heterologous gene product can be enhanced by expressing the gene product in the form of a fusion protein. In this context, the term "fusion protein" denotes a chimeric protein comprising pre-prochymosin, prochymosin or chymosin or at least a milk coagulation active part hereof and, as the fusion partner, at least one amino acid of a different polypeptide. Accordingly, in one embodiment of the invention, the above method is one wherein the nucleic acid sequence codes for a fusion protein comprising pre-prochymosin, prochymosin or chymosin. More specifically, the fusion partner may be glucoamylase or a fragment thereof. In one embodiment the pre-prochymosin, prochymosin or chymosin, or a fusion protein thereof, is secreted over the host cell membrane.

One major objective of the present invention is to provide a method of producing a non-bovine pre-prochymosin, prochymosin or chymosin recombinantly at a high yield. During the experimentation leading to the invention it was a highly unexpected finding that a non-bovine pre-prochymosin, prochymosin or chymosin, when expressed in the same host cell and under essentially identical conditions, is expressed at activity yields which are significantly higher than are the obtained activity yields of bovine chymosin.

In accordance herewith, the above method of the invention is preferably a method wherein the yield of non-bovine pre-prochymosin, prochymosin or chymosin milk clotting activity is at least 10%, 25%, 50%, 100% or 200% higher than the yield of bovine pre-prochymosin, prochymosin or chymosin milk clotting activity obtained when using, under identical production conditions, the same expression vector, but with a coding sequence for bovine pre-prochymosin, prochymosin or chymosin in place of the sequence coding for the non-bovine pre-prochymosin, prochymosin or chymosin.

It is generally known that polypeptides expressed by eukaryotic host organisms may be glycosylated when expressed, the degree of glycosylation depending on the type of polypeptide and host organism. It has been found previously that the milk clotting activity of aspartic proteases of microbial origin that are glycosylated upon expression may be enhanced by subjecting the proteases to a deglycosylating treatment to at least partially remove the sugar moieties attached to the proteases. Such a deglycosylation treatment may e.g. comprise treating the glycosylated protease with an enzyme having a deglycosylating activity including as examples PNGase and endo-β-N-acetylglucosaminidase (EC 3.2.1.96) (Endo-H). Alternatively, the deglycosylation may be obtained by subjecting the glycosylated protease to a chemical treatment, such as treatment with periodate.

Accordingly, in a specific embodiment, the above method comprises, as a further step, that the harvested pre-prochymosin, prochymosin or chymosin is subjected to a deglycosylation treatment.

It is also contemplated that deglycosylation of an expressed pre-prochymosin, prochymosin or chymosin can be obtained in a more direct manner by providing a host cell that in addition to the pre-prochymosin, prochymosin or chymosin expresses a deglycosylating enzyme such as Endo-H whereby the initially glycosylated pre-prochymosin, prochymosin or chymosin is deglycosylated intracellularly or following secretion. Accordingly, in a another embodiment the host cell is a cell further expressing a deglycosylating enzyme capable of deglycosylating co-expressed pre-prochymosin, prochymosin or chymosin.

In another aspect, the invention provides a DNA construct capable of expressing non-bovine pre-prochymosin, prochymosin or chymosin. This construct comprises an expression vector comprising a nucleic acid sequence comprising a gene coding for the pre-prochymosin, prochymosin or chymosin and, operably linked thereto, appropriate expression signals as defined above, permitting the pre-prochymosin, prochymosin or chymosin to be expressed in a host cell. Accordingly, such a construct includes a construct that comprises a sequence coding for a signal peptide for the pre-prochymosin, prochymosin or chymosin and/or an expression signal that is a promoter not natively associated with the coding sequence.

The coding sequence of the DNA construct of the invention can be derived from any of the above non-bovine, i.e. non-*Bos taurus*, animal species including *Camelus dromedarius*. In useful embodiments, the DNA construct comprises a nucleic acid sequence that codes for a fusion protein as also defined above, comprising the pre-prochymosin, prochymosin or chymosin or a fragment hereof having milk clotting activity. In a further embodiment, the the fusion protein comprises glucoamylase or a fragment thereof. The expression vector of the DNA construct may be any of the expression vectors mentioned above including pGAMpR-derived vectors such as the pGAMpR-C vector as described in the below examples. Additionally, the DNA construct according to the invention may further comprise a sequence coding for a deglycosylating enzyme such as endoH.

The sequence of the DNA construct according to the invention that codes for a non-bovine pre-prochymosin, prochymosin or chymosin may be a naturally occurring coding sequence. However, as it will be appreciated by the person of skill in the art, the coding sequence may also be one that is derived from such a naturally occurring coding sequence by one or more silent nucleotide substitution(s), the term "silent" implying that the codon in which the substitution(s) occur codes for the same amino acid as the corresponding codon in the naturally occurring coding sequence.

In a further aspect, the invention provides a host cell transformed with a DNA construct as described above. The host cell is selected from any of the above organisms, i.e. bacterial cells, fungal cells including *Aspergillus niger* var. *awamori* such as the strains deposited as CBS 108915 and CBS 108916., yeast cells, mammalian cells, insect cells and plant cells.

In a still further aspect a milk clotting composition is provided comprising a non-bovine prochymosin or chymosin as defined herein and produced by the above method including such a prochymosin or chymosin that is in a substantially deglycosylated form. Such a composition may, in addition to the active milk clotting enzyme, comprise additives that are conventionally used in rennets of animal origin such as e.g. NaCl. In preferred embodiments, the composition comprises pre-prochymosin, prochymosin or chymosin derived from the group consisting of a Camelidae species, a buffalo species, an ovine species or a caprine species.

The recombinant non-bovine pre-prochymosin, prochymosin or chymosin as provided herein is useful as a milk coagulant product. Accordingly, an important objective of the invention is to provide a method of manufacturing cheese, comprising adding a milk clotting effective amount of the above composition to milk and carrying out appropriate further cheese manufacturing steps. The pre-prochymosin, prochymosin or chymosin of the invention is suitable for cheese manufacturing processes wherein the milk is selected from cow's milk, camel milk, buffalo milk, goat's milk and sheep's milk.

An aspartic protease such as chymosin that is suitable for cheese manufacturing should have a high specific milk clotting activity (C) and a low general, i. e. non-specific, proteolytic activity (P) with regard to milk proteins. Accordingly, the C/P ratio should preferably be as high as possible, as a relatively high P-value, during the cheese manufacturing pro??cess and during maturation of the cheese will lead to the formation of low molecular peptides and free amino acids, which in turn may confer to the finished cheese an undesirable bitter taste and also result in a loss of cheese yield. As used herein, the term "C/P ratio" is defined by the methods for determining a C-value and a P-value, respectively as described in the below examples.

As shown in the below Examples, the use of a recombinantly produced non-bovine prochymosin or chymosin in cheese manufacturing results in a higher yield of cheese than the yield obtained with the same amount of milk clotting activity of bovine prochymosin or chymosin. Accordingly, in one embodiment the invention provides a cheese manufacturing method wherein the yield of cheese obtained is higher than the yield obtained under identical manufacturing conditions using the same amount of bovine prochymosin or chymosin.

It is demonstrated in the below examples, that the non-bovine pre-prochymosin, prochymosin or chymosin has a higher C/P ratio, relative to the conventionally used bovine chymosin. Accordingly, the invention pertains in yet another aspect to a method of manufacturing cheese, comprising adding a milk clotting effective amount of a non-bovine prochymosin or chymosin to the milk including bovine milk and carrying out appropriate further cheese manufacturing steps, the non-bovine prochymosin or chymosin having in said milk a C/P ratio in the range of 2-20, preferably a C/P ratio of at least 3, such as at least 5 or even at least 10.

In one specific embodiment such a pre-prochymosin, prochymosin or chymosin is derived from *Camelus dromedarius*.

It is a further objective of the invention to provide a milk clotting composition comprising a milk clotting bovine enzyme selected from prochymosin, chymosin and pepsin and a non-bovine milk clotting enzyme selected from prochymosin, chymosin and pepsin including such a composition where the milk clotting activity ratio between the bovine and the non-bovine milk clotting enzyme is in the range of 1:99 to 99:1, including a composition where at least 2% of the milk clotting activity is from the non-bovine enzyme such as at least 5%, 10%, 20%, 50%, 75, 90 or 98% of the activity. In one preferred embodiment, the non-bovine enzyme in such a mixed composition is derived from *Camelus dromedarius*.

There is also provided a method of manufacturing cheese from milk including cow's milk, camel's milk, buffalo milk, goat's milk, sheep's milk and a mixture of any such milk types, comprising adding a milk clotting effective amount of the above composition and carrying out appropriate further cheese manufacturing steps.

The invention will now be described in further details in the following, non-limiting examples and the drawings where:

Figure 9:
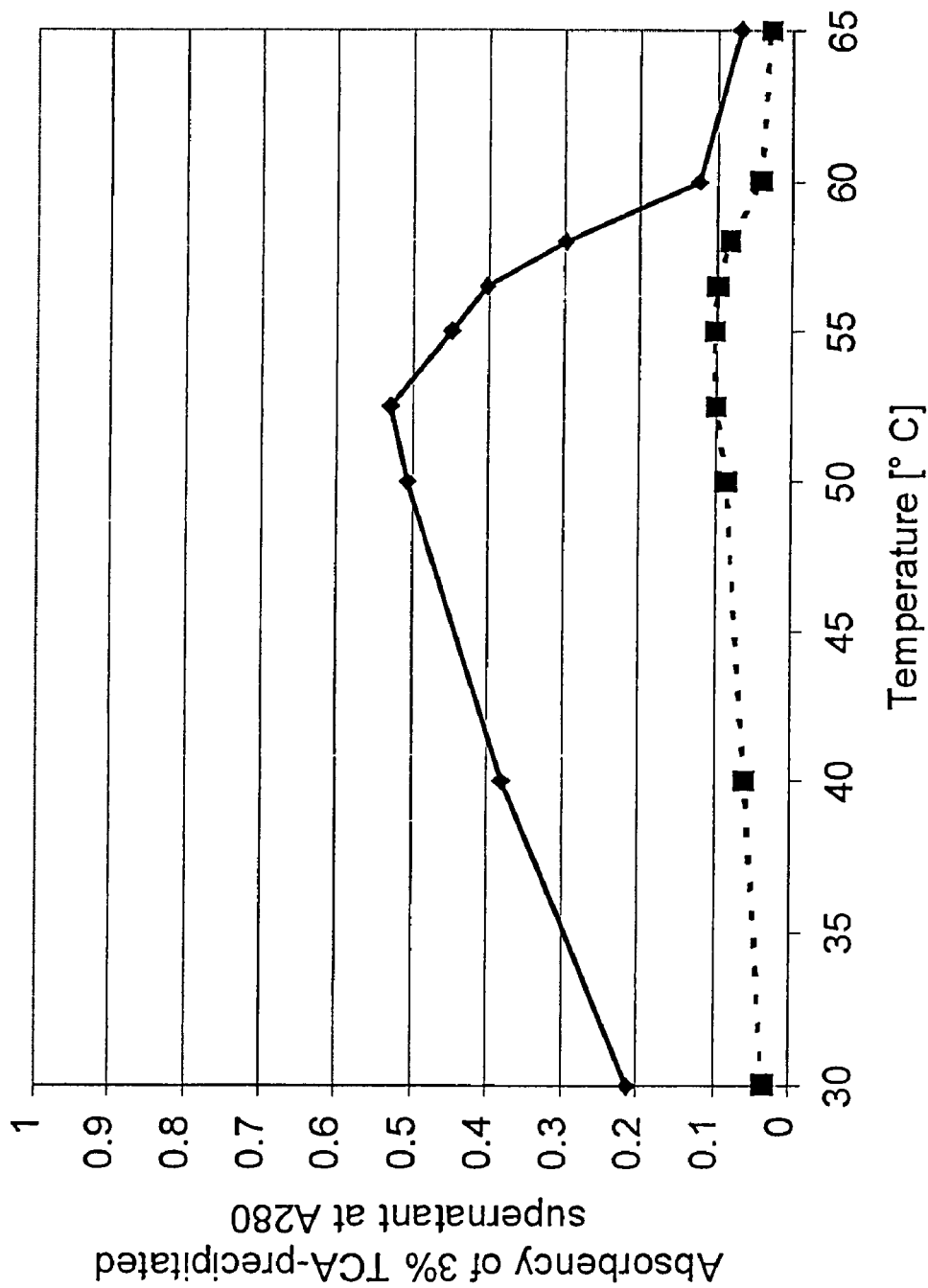
Figure 10:
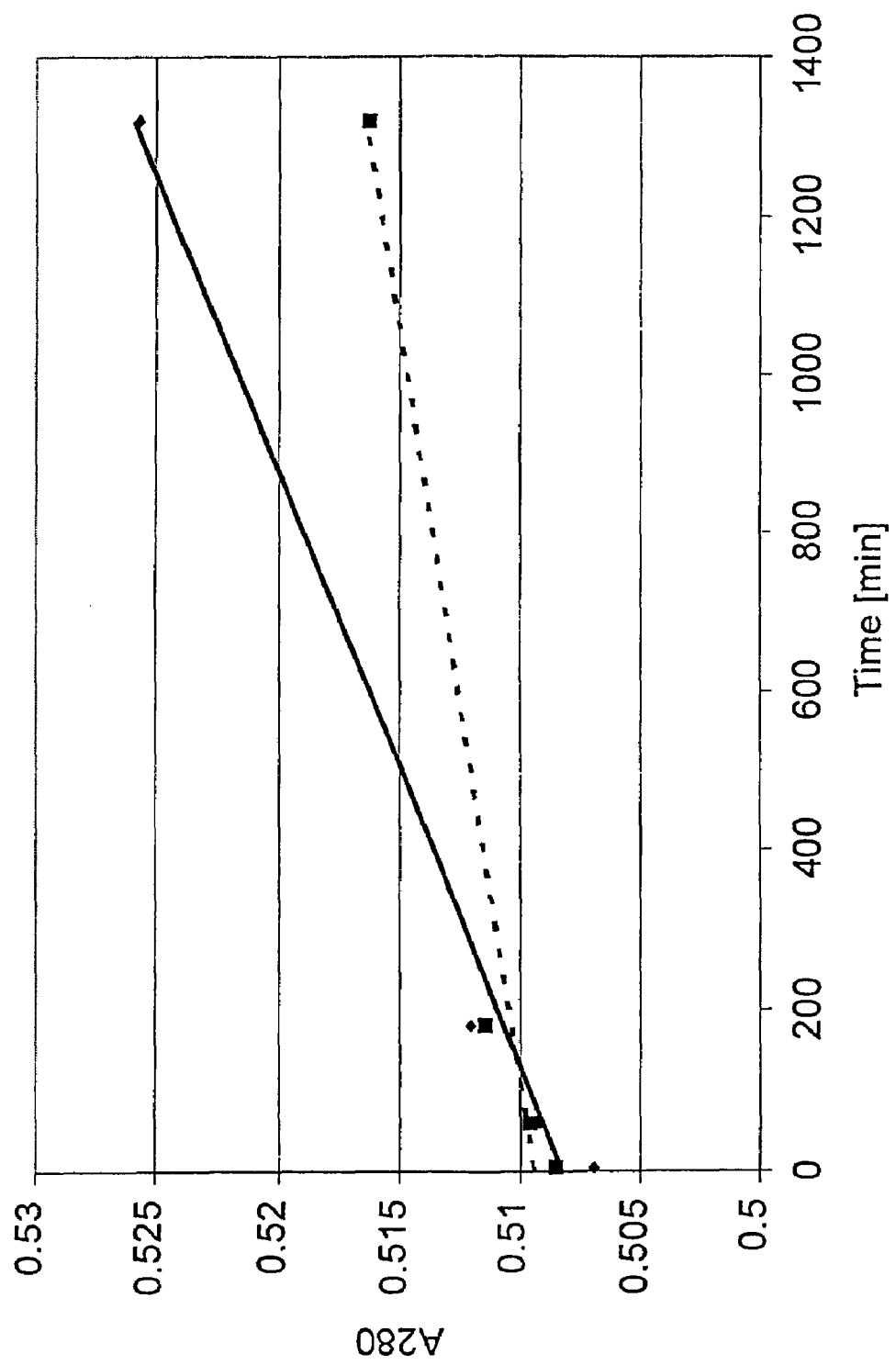

FIG. 9 illustrates the general, non-specific proteolytic activity as absorbancy of 3% TCA-precipitated supernatant of 100 nM recombinantly produced camel chymosin (■------■) and bovine chymosin (♦------♦), respectively in 33 nM MES, pH 5.80 using 0.5% N,N-demethylated bovine casein as the substrate and incubating at 32° C. for 30-180 min. at different temperatures; and FIG. 10 shows peptide and protein concentration in 50 μl of the soluble phase of a coagulum of reconstituted bovine skimmed milk coagulated for 5, 60 and 1320 min., respectively with 65 mlMCU $ml^{-1}$ recombinantly produced camel chymosin (■------■) and bovine chymosin (♦------♦), respectively, measured as absorbancy at 280 nm, and diluted in 950 μl of 8M guanidine-HCl.

EXAMPLE 1

Construction of a Vector for the Expression of Camel Chymosin

Unless indicated otherwise, recombinant DNA techniques were according to Sambrook et al., 1989.

1.1 Cloning of *Camelus dromedarius* Chymosin Gene

A DNA sequence containing a camel prochymosin (cd-prochymosin) coding sequence and adjacent 5' and 3' sequences of the pGAMpR vector (Ward et al., 1990) was amplified by PCR. The pGAMpR vector comprises, as a selection marker, the pyr4 gene of *Neurospora crassa*, which is capable of complementing a pyrG mutation in a recipient strain. mRNA was isolated from mucosal tissue of a 3 year old camel using a direct mRNA Kit (Quiagen, D-40724 Hilden, Germany). Based on this isolated mRNA, a cDNA template for PCR was generated by reverse transcription. For PCR amplification the following pair of primers were used:

cd-prochymosin forward:
 PmlI
 5'-cacgtggcggAGTGGGATCACCAGGATCCCTCTG-3'
  (SEQ ID NO:1)
cd-prochymosin reverse:
 XbaI
 5'-tctagaggaTCAGATGGCCTTGGCCAGCCCCACG-3'
  (SEQ ID NO:2)

The PCR product was ligated into a pCR-script vector (Stratagene, La Jolla, Calif.) according to the manufacturer's recommendations.

1.2 Construction of cd-prochymosin Expression Vector, pGAMpR-C

For construction of pGAMpR-C, a SpeI-XbaI fragment containing a fusion between the *Aspergillus niger* glucoamylase and the *Bos taurus* prochymosin coding sequences was isolated from pGAMpR. This fragment was cloned into pBluescript-SK II+, resulting in vector pSK-SpXb.

Figure 1:
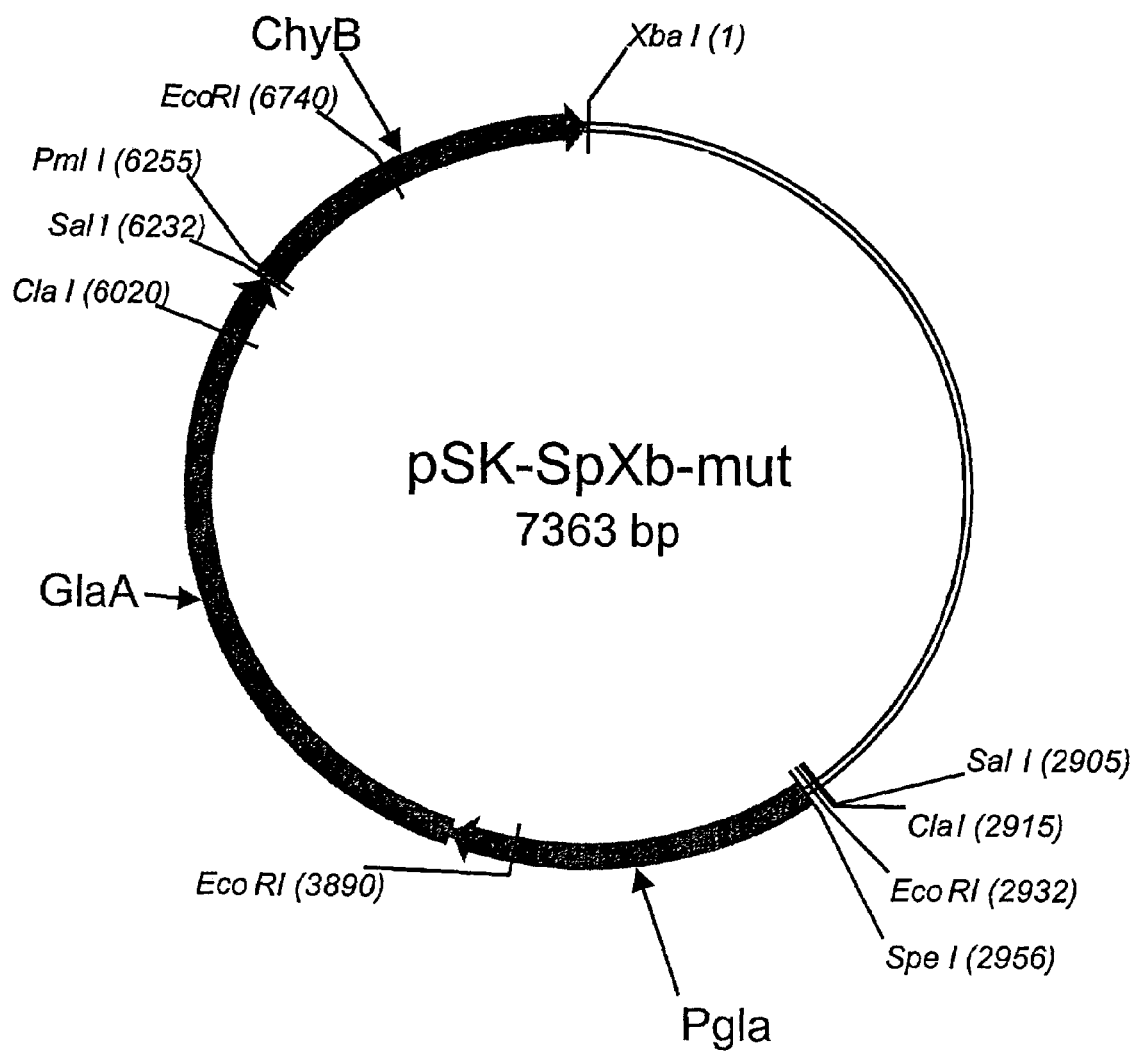
FIG. 1 is a map of plasmid pSK-SbXb-mut containing a glucoamylase A-chymosin B expression cassette. A silent mutation results in a unique PmlI site.

A silent mutation was introduced into pSK-SpXb by oligonucleotide-based mutagenesis in the 3'-region of the glucoamylase to create a unique site for PmlI, resulting in plasmid pSK-SpXb-mut (FIG. 1). The following pair of oligonucleotide primers was used (bases introducing the mutation in the vector are shown in capitals):

5'-gcgacggtgactgacacGtggcgggcagaaata (SEQ ID NO: 3) ac-3' (PmlI mutation forward)

5'-gttatttctgcccgccaCgtgtcagtcaccgtc (SEQ ID NO: 4) gc-3' (PmlI mutation reverse)

Figure 2:
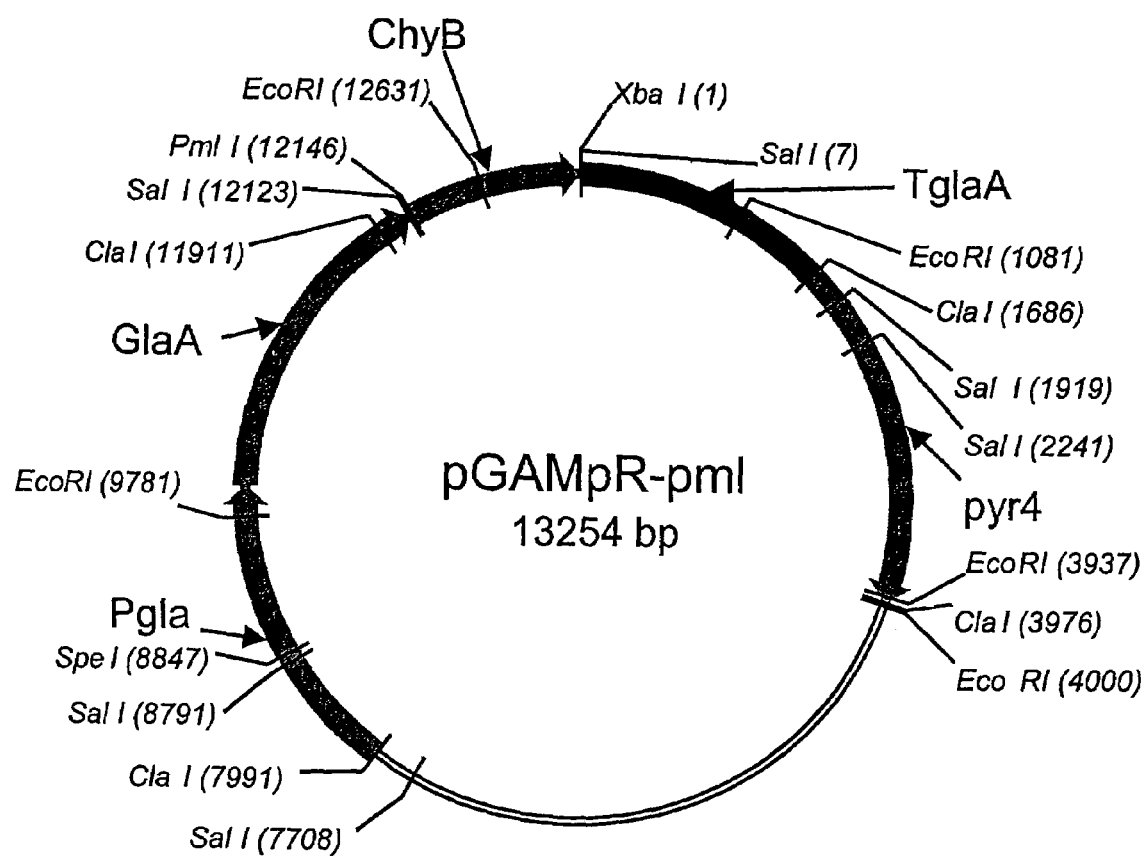
FIG. 2 is a map of plasmid pGAMpR-pmI which is identical to plasmid pGAMpR except for a silent mutation resulting in a unique PmlI site.
Figure 3:
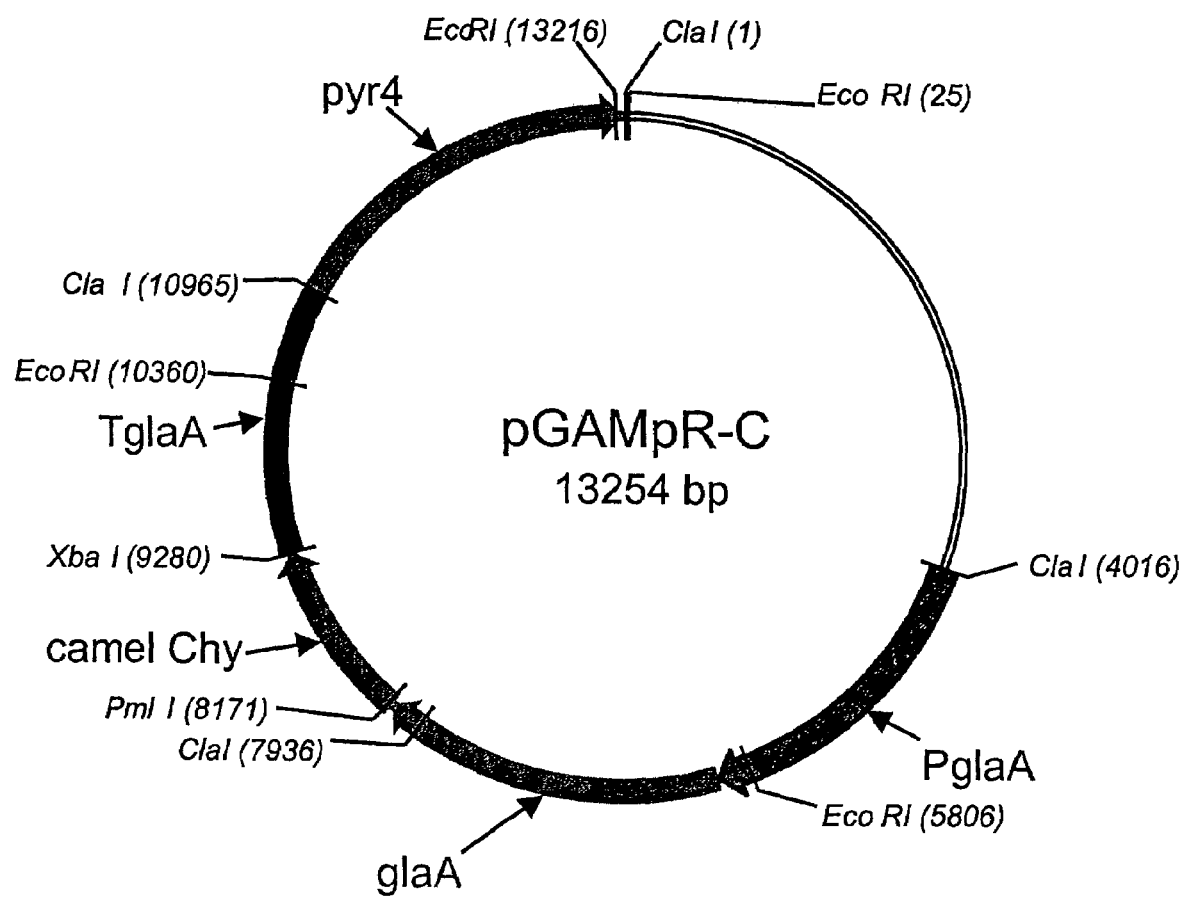
FIG. 3 is a map of plasmid pGAMpR-C, a camel chymosin expression construct.

The SpeI-XbaI fragment from pSK-SpXb-mut was used to replace the corresponding fragment in pGAMpR, resulting in pGAMpR-pmI (FIG. 2). pGAMpR-pmI was digested with PmlI and XbaI and the camel cDNA clone, digested with the same restriction enzymes, was inserted, resulting in pGAMpR-C (FIG. 3). The sequence of the glucoamylase-camel prochymosin fusion in pGAMpR-C was confirmed on both strands.

Accordingly, the Aspergillus expression vector plasmid pGAMpR-C is identical to pGAMpR, the expression plasmid used for expression of bovine chymosin, except that the prochymosin coding sequence is that isolated from *Camelus dromedarius*. When expressed and secreted, the camel prochymosin is converted into chymosin by autocatalytical cleavage of the pro-sequence.

EXAMPLE 2

Transformation of *Aspergillus niger* var. *awamori* with pGAMpR-C

For these transformation experiments, a derivative of *Aspergillus niger* var. *awamori*, strain dgr246pyrG (Ward et al., 1993) was used as recipient. This strain is a derivative of *Aspergillus niger* var. *awamori* strain GCI-HF1-2dgr246 having a pyrG mutation, rendering the strain incapable of growing in the absence of uridine, and which comprises several copies of the pGAMpR plasmid. The derivative strain, dgr246pyrG used as recipient is derived by curing the pyrG mutant parent strain for all copies of pGAMpR.

The dgr246pyrG strain has been deposited under the Budapest Treaty with the Centraal-bureau voor Schimmelcultures (CBS), Oosterstraat 1, P.O. Box 273, 3740 AG Baarn, The Netherlands, on 13 Jun. 2000 under the accession No. CBS 108914.

An optimised protocol as developed by Chr. Hansen A/S was applied for transformation of the "cured" *Aspergillus* strain. This protocol comprises the steps of providing a liquid culture medium, propagation of fungal biomass, generation of protoplasts and transformation including regeneration of protoplasts and selection of transformants.

2.1 Propagation of Fungal Biomass 50 ml of CSL medium [per litre: corn steep liquor, 100 g; $NaH_2PO_4.2H_2O$, 1 g; $MgSO_4$, 0.5 g; Mazu antifoaming agent, 2 g, maltose, 100 g, glucose, 10 g, fructose, 50 g, water 736.5 g] is added to a sterile 250 ml flask, 0.5 ml penicillin/streptomycin supplement (Gibco-BRL #15140-114)] is added and the medium inoculated with $10^6$ spores per ml. The inoculated medium is cultivated overnight at 34-37° C. at 200-250 rpm to obtain a dense suspension of mycelium. 10 ml of this pre-culture is transferred to 100 ml complete *Aspergillus* medium in a 500 ml flask without baffles, incubation overnight at 34-37° C. at 200-250 rpm to obtain a mycelial biomass.

2.2 Generation of Protoplasts

Mycelium as obtained in the above step is filtered over sterile myracloth, washed with sterile water and subsequently with 1700 mOsmol $NaCl/CaCl_2$ (0.27 M $CaCl_2.2H_2O$, 39.7 g/l; 0.58 M NaCl, 33.9 g/l), gently squeezed dry and transferred to a Falcon tube to determine the weight and left to stand on ice.

20 ml 1700 mOsmol $NaCl/CaCl_2$ per g mycelium is added to resuspend the mycelium followed by adding 50 mg Sigma L-1412 *Trichoderma harzianum* Lytic Enzyme per g mycelium dissolved in a small volume of 1700 mOsmol $NaCl/CaCl_2$, incubation in an Erlenmeyer flask at 100 rpm, 37° C. for about 4 hrs during which period the mycelium is repeatedly resuspended every 30 minutes.

When good protoplasting is obtained, i.e. many free protoplasts occur and with hardly any intact mycelium left, the mixture is filtered on ice, using Mesh sheet or myracloth and an equal volume of ice cold STC1700 (1.2 M sorbitol, 218 g/l; 35 mM NaCl, 2.04 g/l; 10 mM Tris.HCl pH 7.5 and 50 mM $CaCl_2.2H_2O$, 7.35 g/l) is added. The number of protoplasts is counted using a glass Bürger-Türk chamber. The protoplast suspension is spun using a bench top centrifuge at 2,000 rpm at 4° C. The resulting pellet is resuspended very gently in 20 ml ice cold STC1700. This washing procedure is repeated twice and the final pellet is resuspended in ice cold STC1700 to a final concentration of about $1 \times 10^8$ protoplasts per ml followed by adjustment to $1 \times 10^8$ protoplasts per ml.

2.3 Transformation

200 µl ($2 \times 10^7$ protoplasts), 2 µl of 0.5 M ATA (0.5 M aurine carboxylic acid (Sigma) in 20% ethanol) and DNA (comprising a marker) up till 15 µl, typically 5-10 µg of DNA, is mixed in a 12 ml test tube. As control a corresponding mixture, but without DNA is used. The transformation mixtures are incubated on ice for 25 min. followed by adding a first drop of 250 µl PTC (60% PEG 4000; 10 mM Tris.HCl pH 7.5; 50 mM $CaCl_2$) by tipping the tube a couple of times without letting the mixture touch the lid and a second drop of 250 µl, mixing and adding 850 µl followed by mixing. Each tube is incubated at room temperature exactly 20 min. followed by filling the tubes with ice cold STC1700 and mixing by reverting the tubes. The mixture is centrifuged for 8-10 min. using a bench top centrifuge at 2000 rpm at 4° C. The resulting pellet is dissolved gently in about 400-800 µl STC1700.

2.4 Regeneration and Selection of Transformants

The transformation mixture is spread onto solid selective regeneration medium plates containing per l medium: agar, 15; sorbitol, 218 g; AspA salts 50× (per litre: 300 g $NaNO_3$, 26 g KCl, 76 g $KH_2PO_4$, 18 ml 10 M KOH, pH about 6.5); glucose 50%, 20 ml; Gibco-BRL #15140-114 Pen-Strep, 10 ml; $MgSO_4$, 2 ml; trace elements (2.2 g $ZnSO_4$, 1.1 g $H_3BO_3$, 0.5 g $MnCl_2.7H_2O$, 0.5 g $FeSO_4.7H_2O$, 0.17 g $CoCl_2.6H_2O$, 0.16 $CuSO_4.5H_2O$, 0.15 $NaMoO_4.2H_2O$, 5 g EDTA, water to 100 ml, pH 6.5), 1 ml. The plates are incubated at 37° C. for 5-10 days and transformants selected.

About 80 transformants were obtained and spores of these transformants were obtained.

EXAMPLE 3

Production of Camel Chymosin Using Recombinant *Aspergillus niger* var. *awamori*

3.1 Selection of Transformants Producing High Amounts of Chymosin

To select the transformants that produced the most chymosin, a small scale (20 ml) shake flask experiments with 45 transformants was carried out. 20 ml of CSL medium (see above) was inoculated with $1\times10^8$ spores of each transformant, incubation 24-48 hrs at 37° C. and 200 rpm. 2 ml of these precultures was used for inoculation of 20 ml medium followed by incubation for 10 days at 37° C., 200 rpm. After incubation the cultures were centrifuged at 14,000 rpm using an Eppendorf centrifuge and the clear supernatants were collected and stored at -20° C. until determination of chymosin activity. As controls, both the recipient strain and an *Aspergillus niger* var. *awamori* production strain for bovine chymosin, dgr246chlor25 (Dunn-Coleman et al., 1991) containing the pGAMpR (spores of this strain used as inoculum material is referred to herein as PIM2075) were included.

Figure 4:
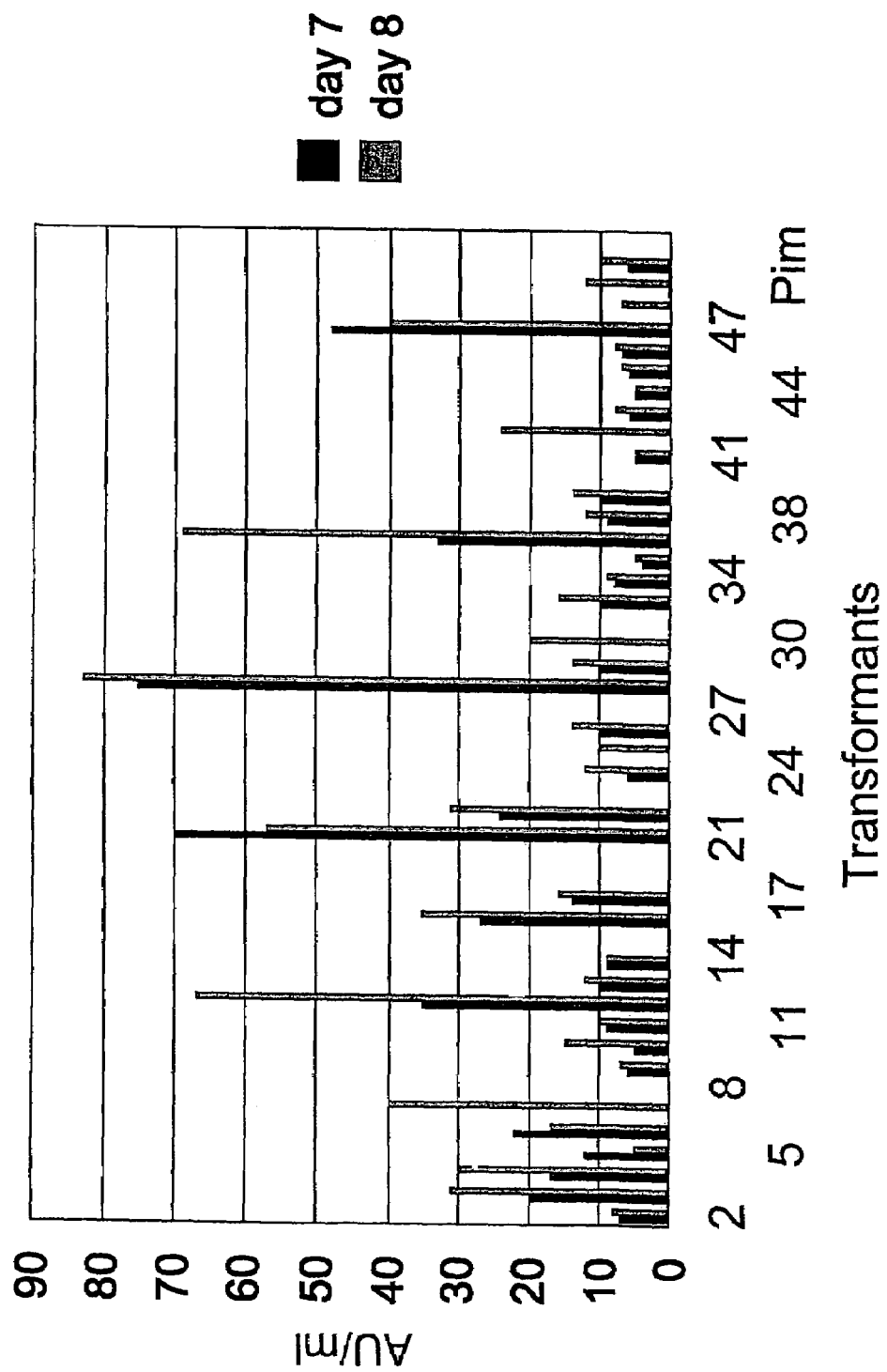
FIG. 4 shows the milk clotting activity in arbitrary units in supernatants of plasmid pGAMpR-C transformed *Aspergillus niger* var. *awamori* cultivated in shake flasks in CSL medium for 24-48 hrs at 37° C. and 200 rpm.

The results of these experiments are summarised in FIG. 4. It appears that 5 of the tested strains produced in excess of 40 arbitrary units per ml supernatant. Among the tested transformants, the best producers were strains #21 and #28.

A sample of the strains #21 and #28 were deposited under the Budapest Treaty with the Centraalbureau voor Schimmelcultures (CBS), Oosterstraat 1, P.O. Box 273, 3740 AG Baarn, The Netherlands, on 13 Jun. 2000 under the accession Nos. 108915 and 108916, respectively.

A colony PCR experiment was carried out to verify that the chymosin produced by the transformants in fact was camel chymosin. Mycelium of the transformants was analysed using two primer sets, one specific for bovine chymosin and one specific for camel chymosin. It was confirmed that all transformants only contained the *Camelus dromedarius* gene in that no bands were observed in any of the transformants using the bovine primer set, but bands were generated in all of the transformants when the camel chymosin primer set was used. Both the cured recipient strain and the bovine chymosin production strain were tested similarly. No bands could be observed with either primer set when the cured strain was tested whereas the control production strain yielded PCR products only with the bovine chymosin primer set.

3.2 Pilot Scale Production of Camel Chymosin

The two best produces from the above small scale screening procedure were tested further for their chymosin production capabilities in 19 l Bioengineering NLF22 fermentors. As a control, an *Aspergillus niger* var. *awamori* strain transformed with pGAMpR, referred to as PIM2075 was tested similarly.

The basic medium used in this experiment had the following composition per litre: Dan-pro™ soya, 44.68 g; $KH_2PO_4$, 1.06 g; Mazu DF204K antifoaming agent, 1.00 g; $MgSO_4 \cdot 7H_2O$, 2.07 g; $NaH_2PO_4 \cdot 2H_2O$, 1.20 g; $(NH_3)_2PO_4$, 17.29 g; $H_2SO_4$ 38%, 0.80 ml, water to 1 litre. A 35% aqueous solution of maltose was used as the carbon source and to maintain the pH at the pre-set value, a 25% $NH_3$ solution was used. The fermentation parameters were the following: pH: 5.5; temperature: 35° C.; agitation: 600 rpm; air supply: 12 l per min.; overpressure: 0.5 bar.

Figure 5:
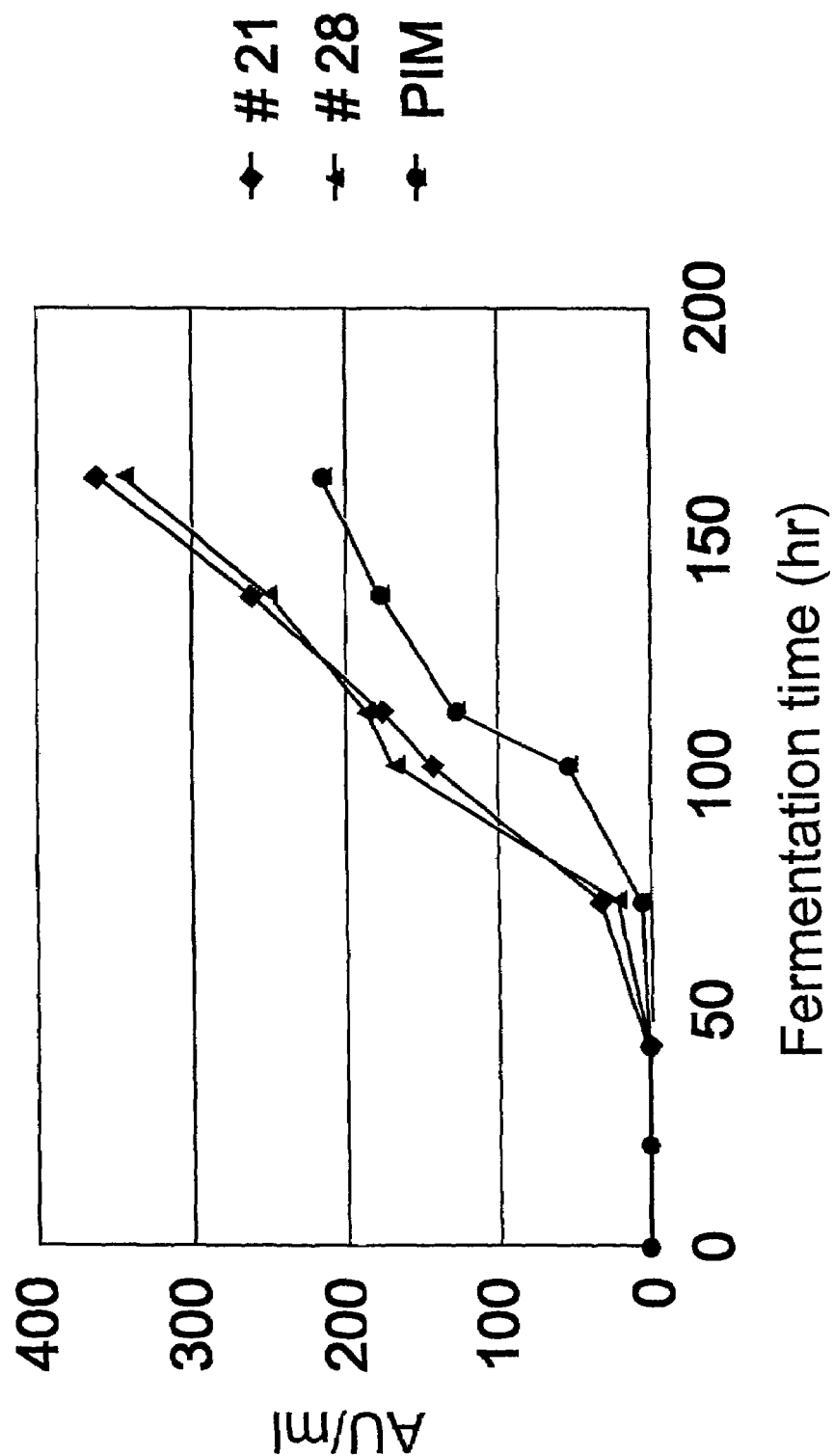
FIG. 5 shows the production of camel chymosin activity in pilot scale fermentation of pGAMpR-C transformed *Aspergillus niger* var. *awamori* strain #21 and #28 as compared to production of bovine chymosin activity using an *Aspergillus niger* var. *awamori* strain transformed with pGAMpR.

During 164 hrs of fermentation, the concentration of camel and bovine chymosin activity, respectively was determined at intervals in the fermentation broths. The results are summarised in FIG. 5. As it appears, the yield of camel chymosin activity from both transformant strains was, during the entire fermentation period, significantly higher than that of bovine chymosin. At the end of the fermentations, the chymosin milk clotting activity yield of recombinant strains #21 and #28 was 361 and 343 arbitrary units, respectively, whereas the yield of bovine chymosin activity produced by PIM2075 was 215 arbitrary units, i.e. the recombinant strains expressing *Camelus dromedarius* chymosin produced about 70% more chymosin activity than the bovine chymosin producing strain did under identical production conditions.

EXAMPLE 4

Non-specific Proteolytic Activity of Recombinant *Camelus dromedarius* Chymosin

In this experiment, the general (non-specific) proteolytic activity (P-value) of recombinantly produced *Camelus dromedarius* chymosin (Cd chymosin) as obtained in Example 3 on bovine whole casein was studied. For comparison, a recombinantly produced bovine chymosin, Chy-Max™ (Bt chymosin) was included. The P-value was tested over time and the effect on the proteolytic activity of $Ca^{2+}$ and pH, respectively, was studied.

4.1 Assay

Unless otherwise stated, the activity reactions were done under the following conditions: 0.5% N,N-dimethylated bovine casein (Sigma C9801), 100 nM chymosin in 33 nM MES, pH 5.80 at 32° C. for 30 min. to 180 min. The absorbency of 3% TCA supernatants was measured at 280 nm. The conditions for the activity reactions were selected so as to include those of a conventional cheese manufacturing process in respect of substrate to be analysed, concentrations of substrate and enzyme, temperature (30-35° C.), pH (about 6.6), $Ca^{2+}$ concentration (0-2 nM) and reaction time.

4.2 Results

Figure 6:
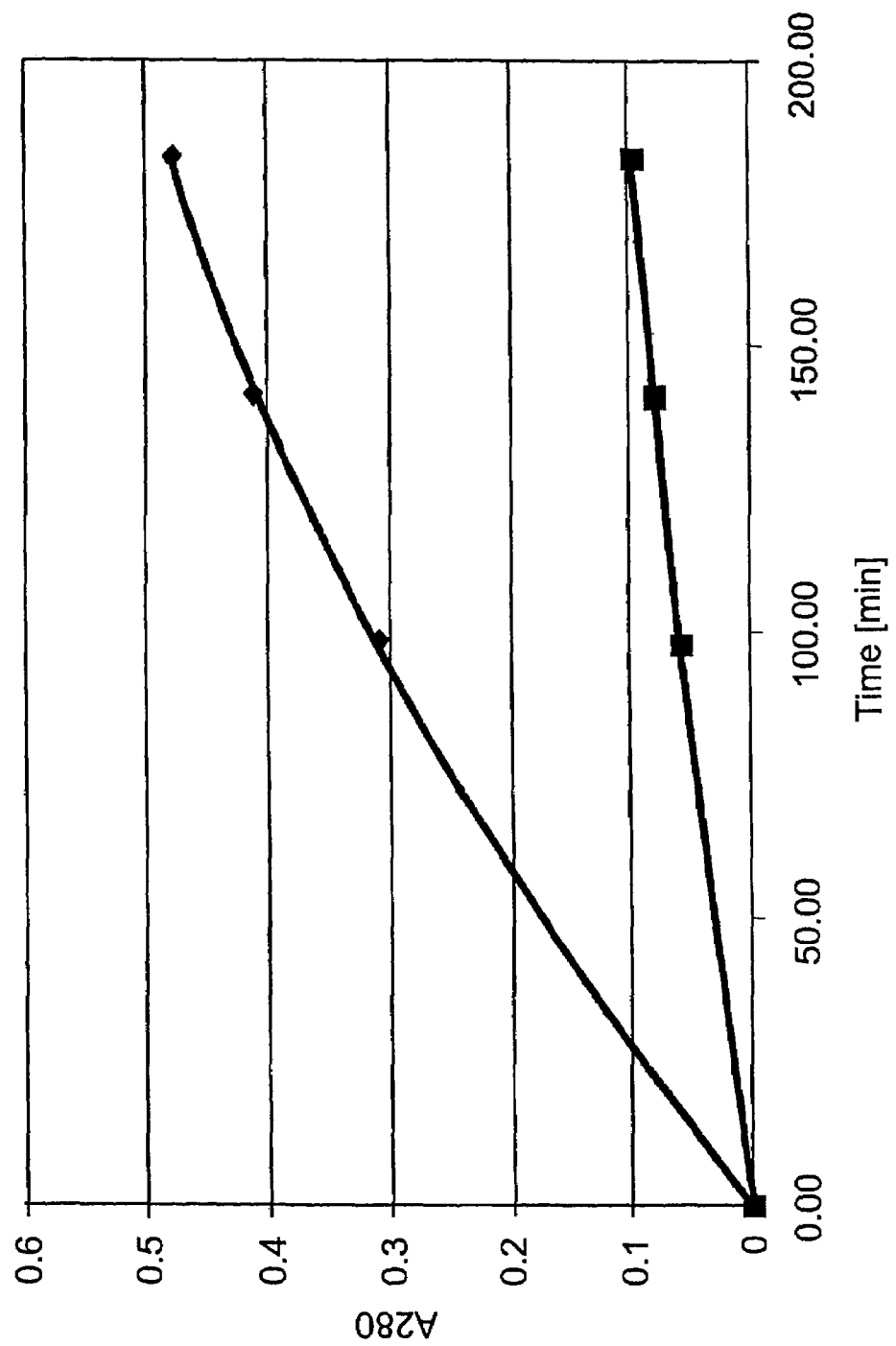
FIG. 6 illustrates the progress of whole casein digestion over time using recombinantly produced camel chymosin (■------■) and bovine chymosin (♦------♦), respectively.

Over a time period of 180 min., the P-value of the Bt chymosin increased progressively to an $A_{280}$ of about 0.5 whereas, during the reaction period the Cd chymosin showed a much lower non-specific proteolytic activity, ending at an $A_{280}$ of about 0.1 (FIG. 6).

Figure 7:
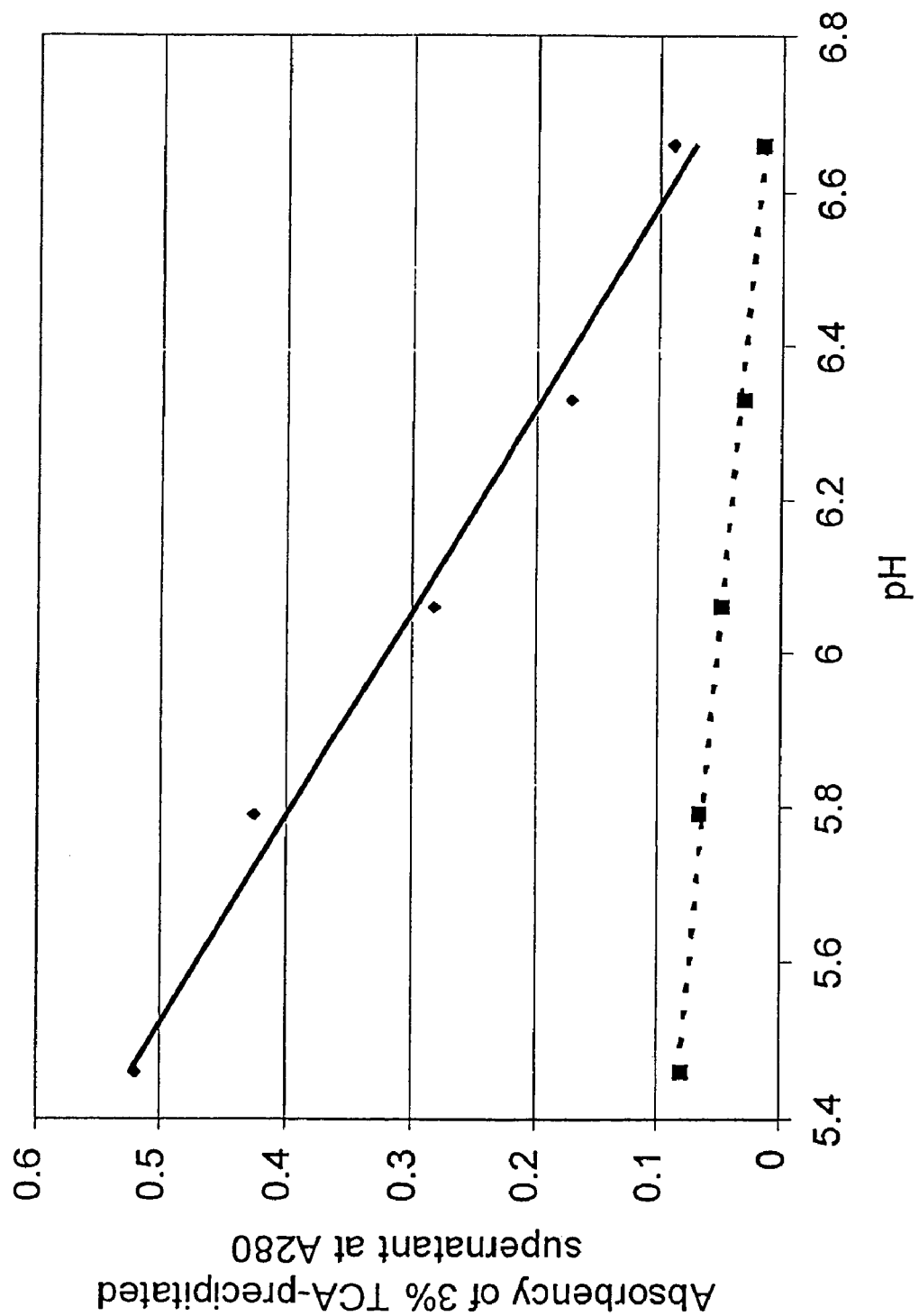
FIG. 7 illustrates the general, non-specific proteolytic activity as absorbancy of 3% TCA-precipitated supernatant of 100 nM recombinantly produced camel chymosin (■------■) and bovine chymosin (♦------♦), respectively in 33 nM MES, pH 5.80 using 0.5% N,N-demethylated bovine casein as the substrate and incubating at 32° C. for 30-180 min. at different pH.
Figure 8:
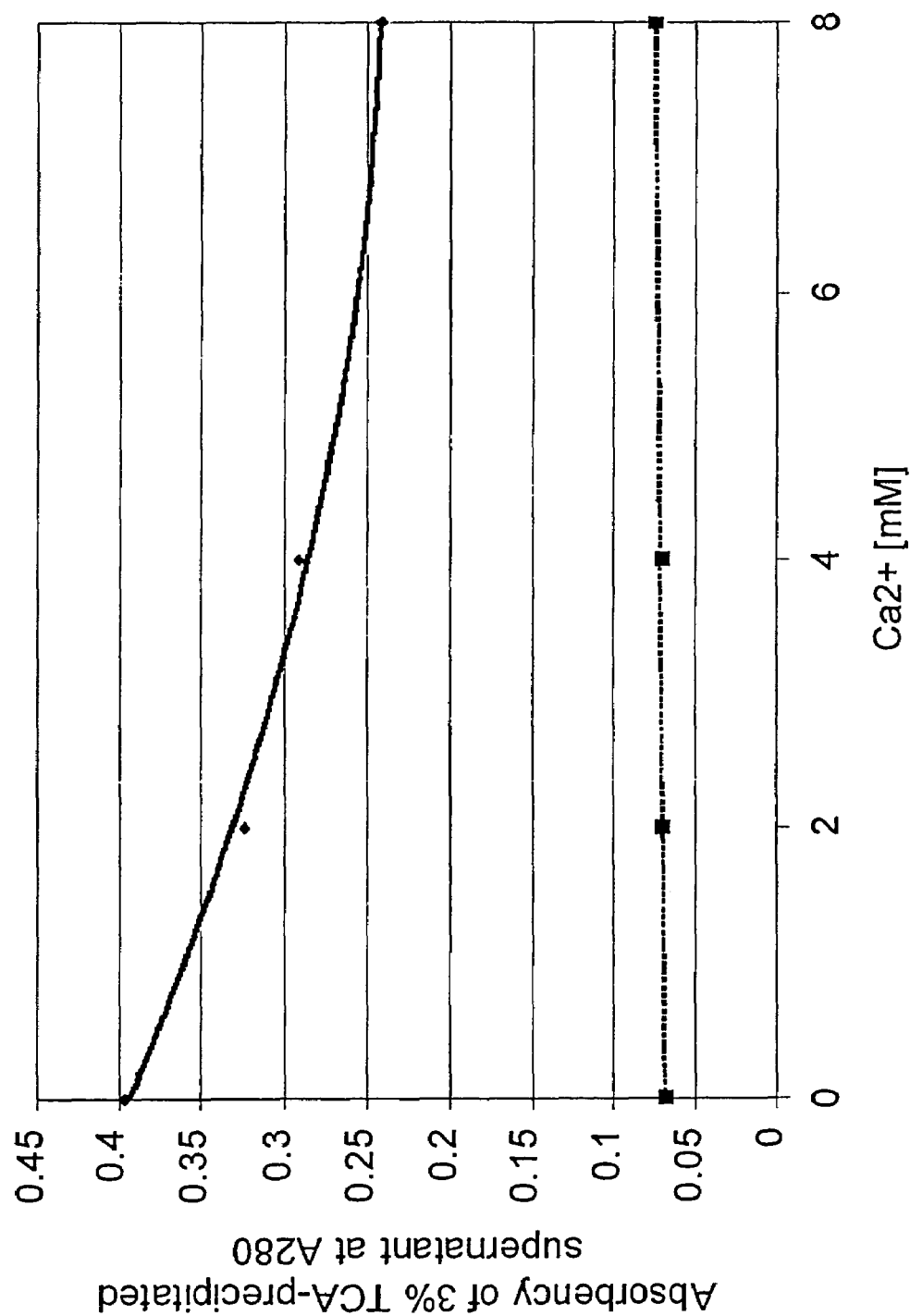
FIG. 8 illustrates the general, non-specific proteolytic activity as absorbancy of 3% TCA-precipitated supernatant of 100 nM recombinantly produced camel chymosin (■------■) and bovine chymosin (♦------♦), respectively in 33 nM MES, pH 5.80 using 0.5% N,N-demethylated bovine casein as the substrate and incubating at 32° C. for 30-180 min. at different $Ca^{2+}$ concentrations.

The effects of pH in the range of 5.4-6.8, $Ca^{2+}$ concentration in the range of 0-8 mM and the temperature in the range of 30-65° C., on the non-specific proteolytic activity of Cd chymosin and Bt chymosin, respectively are summarised in FIGS. 7-9. As it appears, the non-specific proteolytic activity of the *Camelus dromedarius* chymosin was generally significantly lower that that of the bovine chymosin under all test conditions used.

A higher non-specific proteolytic activity was observed when the pH of the assay was lowered (FIG. 7). The relation of the P-values between camel and bovine chymosin remained substantially constant over the pH range studied.

EXAMPLE 5

The Milk Clotting Activity of Recombinant *Camelus dromedarius* Chymosin

In this experiment, the milk clotting activity (C-value) of the recombinant Cd chymosin of the invention was studied at 32° C. using as substrate 10% (w/v) low heat spray-dried bovine skimmed milk (Hochdorf). The concentration of Cd chymosin used was 3.1 nM. For comparison, the C-value of recombinant Bt chymosin (ChyMax™) at a concentration of 5.4 nM (same milk clotting activity in IMCUs as the Cd chymosin) was determined under the same conditions. The milk clotting activity and final curd strength were determined. In addition, the effect of changes in pH and $Ca^{2+}$ concentration on the milk clotting activity of both enzymes was determined. The results of these experiments can be summarised as follows:

The milk clotting activity of the camel chymosin is less affected by changes in pH and $Ca^{2+}$ concentration. The average clotting activity (C) per mole of camel chymosin was about 170% of the activity per mole of the bovine chymosin. Under typical cheese manufacturing conditions as described above, the camel chymosin C-value is about 180% of the corresponding value for bovine chymosin. The final milk curd strength was essentially the same for both enzymes, indicating similar clotting and synthesis reactions.

Based on the results in this Example and those found in Example 4, the C/P ratio for camel chymosin can be estimated, relative to that for bovine chymosin. These data are summarised in the below table 5.1 which also shows corresponding data for porcine chymosin, bovine pepsin B and two microbial aspartic proteases:

TABLE 5.1

Milk clotting activity, non-specific proteolytic activity and C/P value for porcine chymosin, bovine pepsin B and two microbial aspartic proteases:

|  | Milk clotting activity (% of bovine chymosin) | Non-specific proteolytic activity (% of bovine chymosin) | C/P value |
|---|---|---|---|
| Bovine chymosin | 100 | 100 | 1.00 |
| Camel chymosin | 170 | 25 | 7.00 |
| Porcine chymosin | 25 | 12 | 2.10 |
| M. pusillus protease | 33 | 147 | 0.22 |
| M. miehei protease | 19 | 149 | 0.13 |
| Bovine pepsin A | 124 | 2731 | 0.05 |

These data shows that among the listed aspartic proteases, recombinant camel chymosin has the highest milk clotting activity and the second lowest non-specific proteolytic activity on bovine casein, resulting in by far the highest C/P value among these proteases. In particular, it is significant that in respect of these parameters, camel chymosin outperforms the commercial recombinant bovine chymosin significantly.

EXAMPLE 6

Determination of the Amount of Enzymatic Digests and Whey Protein in the Soluble Phase of Milk Coagulum Using Recombinant *Camelus dromedarius* (Cd) Chymosin or ChyMax™ (Bt Chymosin)

10% (w/v) spray-dried bovine skimmed milk was dissolved in 50 mM MES, 1 mM $CaCl_2$, pH 5.6. The milk was coagulated with 65 mlMCU $ml^{-1}$ of the respective recombinant chymosin preparations, i.e. recombinant *Camelus dromedarius* (Cd) chymosin or ChyMax™ (Bt chymosin) for 5, 60, 180 and 1320 min., respectively. The formed coagula were centrifuged at 20,000×g at 4° C. for 5 min. Fifty μl of the supernatant containing breakdown products of enzymatic digests and whey proteins was diluted in 950 μl of 8M guanidine-HCl, pH 6.5 and the absorbancy at 280 nm was measured.

The results are summarised in FIG. 10. As it appears, the amount of peptides and protein was highest in supernatants derived from coagulation with the bovine chymosin, indicating that the camel chymosin under milk clotting conditions has less non-specific proteolytic activity than bovine chymosin.

EXAMPLE 7

Coagulation of Raw Cow's Milk and Camel Milk Using Recombinantly Produced Recombinant *Camelus dromedarius* (Cd) Chymosin or ChyMax™ (Bt Chymosin)

Raw milk was stored for two days at 4° C. Milk samples (10 per analysis) were coagulated with 65 mlMCU $ml^{-1}$. The rennet coagulation time (r[min]) and the curd strength of the coagula ($A_{60}$[mm]) were determined. Curd strength was determined using a Formagraph device (Foss Electric, Hillerød, Denmark). The results are summarised in Table 7.1.

Dilutions of camel and bovine chymosin adjusted to the same clotting activity on bovine spray-dried skimmed milk in 1 mM $CaCl_2$ showed activity on raw bovine milk which was similarly higher (shorter rennet coagulation time) for both enzymes, relative to the activity on the spray-dried bovine milk. The strength of the final curd of bovine milk was slightly higher when using the camel chymosin. Bovine chymosin hardly had any renneting activity on raw camel milk, whereas camel chymosin showed a high activity resulting in a curd of medium curd strength.

TABLE 7.1

Rennet coagulation time and curd strength using bovine or camel chymosin

| Enzyme | Milk | r[min] | $A_{60}$[mm] |
|---|---|---|---|
| Bt chymosin | Bovine raw milk | 12.34 | 48.94 |
| Cd chymosin | Bovine raw milk | 12.20 | 50.56 |
| Cd chymosin | Bovine skimmed milk | 22.07 | 37.96 |
| Bt chymosin | Camel raw milk | 59.45 | 0.40 |
| Cd chymosin | Camel raw milk | 12.66 | 18.24 |

EXAMPLE 8

Examination of the Proteolytic Activity of Recombinant *Camelus dromedarius* (Cd) Chymosin and ChyMax™ (Bt Chymosin)

Two synthetic peptidases, which correspond to the chymosin sensitive regions of camel- and bovine κ-casein (CN), were proteolytically cleaved with bovine and camel chymosin, respectively. $K_M$ and $k_{cat}$ were determined at pH 5.6. Additionally, temperature and pH optima of these reactions were measured. The two following synthetic peptides were used in this study:

Synthetic Peptide Corresponding to Bovine κ-CN
$NH_2$-His-Pro-His-Pro-His-Leu-Ser-(p-$NO_2$)Phe∞Met-Ala-Ile-COOH (SEQ ID NO:5)

Synthetic Peptide Corresponding to Camel κ-CN
$NH_2$-Arg-Pro-Arg-Pro-Arg-Pro-Ser-(p-$NO_2$)Phe∞Ile-Ala-Ile-COOH (SEQ ID NO:6)
∞ fissile bond The measurement of samples was repeated 3 to 6 times, the Michaelis-Menten and the turnover values were determined from Lineweaver-Burke plots with weighted linear regression of data.

The results are summarised in Table 8.1

TABLE 8.1

Summary of results

| | Bt Chymosin | Cd Chymosin |
|---|---|---|
| $K_M$ for Bt κ-CN | 0.165 + 0.015/−0.014 mM | 0.077 + 0.019/−0.015 mM |
| $k_{cat}$ for Bt κ-CN | 44.3 + 1.3/−1.2 $s^{-2}$ | 11.7 + 1.5/−1.2 $s^{-1}$ |
| $K_M$ for Cd κ-CN | 0.134 + 0.022/−0.021 mM | 0.056 + 0.035/−0.021 mM |
| $k_{cat}$ for Cd κ-CN | 4.3 + 0.2/−0.1 $s^{-2}$ | 5.1 + 1.7/−1.0 $s^{-1}$ |
| Temp. optimum (Bt κ-CN) | ~42° C. | ~42° C. |
| Temp. optimum (Cd κ-CN) | ~58° C. | ~47° C. |
| pH optimum (Bt κ-CN) | ~4.9 | ~5.1 |

Marked differences were found when the enzymes were examined for proteolytic activity towards two synthetic peptides representing part of the chymosin sensitive regions of bovine and camel κ-casein. The substrate binding of camel chymosin was found to be about double as high (half $K_M$ value) as the substrate binding of bovine chymosin and the turn-over rate of camel chymosin against the bovine κ-CN peptide was about four times lower than the turnover rate of bovine chymosin.

These findings may explain the higher C/P ratio found for camel chymosin in Example 5. Since the fissile bond of κ-CN represents only a small fraction of the fissile sites in milk proteins, a higher specific binding of the target molecule, and a low non-specific proteolytic activity, effecting self-inhibition of the enzyme and subsequent activation by the target molecule, will lead to a high C/P ratio. Furthermore, similar temperature and pH optima were found for proteolysis of the Bt κ-CN peptide, and the temperature optima for the Cd κ-CN peptide were found to be markedly higher, mainly the one of bovine chymosin.

EXAMPLE 9

Determination of the Cheese Yield Using ChyMax™ (FPC) and Camel Chymosin (FPCC)

9.1 Introduction

The effect of milk clotting enzymes on cheese yield is a characteristic of great commercial importance. Careful measurement of the level of dry matter in whey is used as a method of comparing the effect of enzymes on cheese yield. In this study the cheese yield obtained by using the commercial product ChyMax™ (FPC) and the fermented produced camel chymosin (FPCC), both of Chr. Hansen A/S origin, were compared.

9.2 Materials and Methods 9.2.1 Milk Clotting Enzymes

The milk clotting enzymes used were FPC (batch no. 2114475, 198 IMCU/ml) and fermented produced camel chymosin, FPCC, (batch no. SR 30.05.00, 234 IMCU/ml). The amounts used were such that a cutting time of 30 minutes were obtained. Dosages were kept constant throughout the study. Variation in the coagulability of the milk were compensated by varying cutting times.

9.2.2 Cheese Making in Beakers

Whole pasteurised non-homogenised milk from Arla Foods, Slagelse, Denmark, was used. The cheese making procedure is summarised in Table 9.1. 4000 g of milk was added to a 5-litre beaker. GluconoDeltaLactone (GDL) from "DAN BOUQUET" was added in an amount of 3,200 g. 1,600 g of $CaCl_2$ was added. Cutting took place after about 30 min. Curd and whey were transferred to cheesecloth after healing and stirring for 30 min, and left to drain overnight. Both milk clotting enzymes were used in each of the 16 trials.

9.2.3 Sampling and Analysis

Well mixed total whey was filtered through a layer of gauze to remove cheese dust. Dry matter was determined by drying about 25 g of whey on lapis pumices p.a. for 4 hours at a temperature of 110° C. The analyses were done in duplicate.

9.2.4 Statistical Analysis

A paired students t test was used on n=16 differences in total dry matter of the whey, using $$t = x_{mean}/(s_2/n)_{1/2}$$

as an estimate, $$t_{16}(90\%)=1.34,\ t_{16}(95\%)=1.75,\ t_{16}(99.5\%)=2.92$$

9.3 Results and Discussion

Table 9.1 summaries some parameters for the cheese making procedure. Recovery of milk as cheese and whey was over 99%. Clotting activity of 140 IMCU FPC and 140 IMCU FPCC, respectively, were used for all beakers. Cutting time was in average 30 min.

TABLE 9.1

Cheese making parameters

| | Parameter | n | s |
|---|---|---|---|
| | mean | | |
| Milk coagulating enzyme IMCU/4 | Milk, amount in g  4000 | 16 | constant |
| | GDL in g  3,200 | 16 | constant |
| | FPC | 8 | constant |
| | FPCC | 8 | constant |
| | $CaCl_2$/g  1,60 | 16 | |
| | Time, min. | | |
| | acidification  30 | | constant |
| | cutting time  2 | | |
| | healing time  3 | | constant |
| | stirring  25 | | constant |
| | scooping  1 | | constant |
| | scooping to press  60 | | constant |
| | pH | | |
| | milk  6.66 | | |
| | setting  6.40 | | |
| | whey  n.d | | |
| | Temperature, ° C. | | |
| | setting  31.5 | | |
| | Weights, g | | |
| | milk  4000 | | constant |
| | whey  3350 | | |
| | curd  610 | | |

Table 9.2 summaries the results on the individual cheese trials, in particular dry matter (DM) in the whey, with delta-dry-matter calculated as the difference between FPC amount of whey times DM % deducting FPCC amount of whey times DM %. Average dry a matter was found to be 221.4156 g in FPC whey and 221.8666 g in FPCC whey.

Lønblad, P. and Foltmann, B. (1996) The Primary Structure and Enzymic Properties of Porcine Prochymosin and Chymosin, Int. J. Biochem. Cell Biol. 28:667-675.

TABLE 9.2

Results of the individual cheese trials

| No. | Date | Type of rennet | Recovery | Dry matter in whey (%) | Total dry matter in whey | Delta dry matter | Delta total dry matter |
|---|---|---|---|---|---|---|---|
|   | 28.11.00 | FPC | 98.69 | 6.639 | 221.32 |   |   |
| 1 | 28.11.00 | FPCC | 98.74 | 6.606 | 220.71 | 0.03304 | 0.60581 |
|   | 29.11.00 | FPC | 98.89 | 6.685 | 222.14 |   |   |
| 2 | 29.11.00 | FPCC | 99.00 | 6.681 | 222.66 | 0.00433 | -0.51101 |
|   | 30.11.00 | FPC | 98.38 | 6.641 | 220.62 |   |   |
| 3 | 30.11.00 | FPCC | 98.62 | 6.602 | 220.85 | 0.03898 | -0.22351 |
|   | 04.12.00 | FPC | 99.27 | 6.610 | 223.60 |   |   |
| 4 | 04.12.00 | FPCC | 98.87 | 6.628 | 223.22 | -0.01807 | 0.38949 |
|   | 05.12.00 | FPC | 98.80 | 6.613 | 222.36 |   |   |
| 5 | 05.12.00 | FPCC | 98.71 | 6.635 | 222.41 | -0.02205 | -0.04471 |
|   | 06.12.00 | FPC | 99.02 | 6.446 | 217.65 |   |   |
| 6 | 06.12.00 | FPCC | 98.95 | 6.570 | 221.32 | -0.12420 | -3.67446 |
|   | 07.12.00 | FPC | 98.81 | 6.365 | 213.15 |   |   |
| 7 | 07.12.00 | FPCC | 98.61 | 6.442 | 214.95 | -0.07644 | -1.79965 |
|   | 12.12.00 | FPC | 98.81 | 6.520 | 218.35 |   |   |
| 8 | 12.12.00 | FPCC | 98.61 | 6.508 | 217.15 | 0.01279 | 1.19616 |
|   | 13.12.00 | FPC | 98.88 | 6.611 | 223.18 |   |   |
| 9 | 13.12.00 | FPCC | 98.82 | 6.614 | 222.48 | -0.00290 | 0.70228 |
|   | 15.12.00 | FPC | 98.78 | 6.665 | 222.37 |   |   |
| 10 | 15.12.00 | FPCC | 98.87 | 6.688 | 223.31 | -0.02258 | -0.94070 |
|   | 20.12.00 | FPC | 98.23 | 6.685 | 221.63 |   |   |
| 11 | 20.12.00 | FPCC | 98.26 | 6.636 | 219.32 | 0.04856 | 2.31351 |
|   | 21.12.00 | FPC | 98.13 | 6.46 | 215.13 |   |   |
| 12 | 21.12.00 | FPCC | 98.40 | 6.50 | 217.58 | -0.04364 | -2.45507 |
|   | 16.01.01 | FPC | 98.70 | 6.752 | 223.83 |   |   |
| 13 | 16.01.01 | FPCC | 98.73 | 6.814 | 226.32 | -0.06126 | -2.49389 |
|   | 17.01.01 | FPC | 98.73 | 6.801 | 226.43 |   |   |
| 14 | 17.01.01 | FPCC | 98.73 | 6.747 | 225.99 | 0.05351 | 0.43229 |
|   | 18.01.01 | FPC | 98.49 | 6.695 | 221.48 |   |   |
| 15 | 18.01.01 | FPCC | 98.63 | 6.725 | 222.01 | -0.02969 | -0.52480 |
|   | 09.02.01 | FPC | 98.88 | 6.867 | 229.39 |   |   |
| 16 | 09.02.01 | FPCC | 99.08 | 6.854 | 299.58 | 0.01354 | -0.18775 |
|   |   | FPC | AVG | 6.628 | 221.4156 | -0.0123 | -0.4510 |
|   |   | FPCC | AVG | 6.641 | 221.8666 |   |   |
|   |   |   |   |   | $S_2$ | 0.0467 | 1.4837 |

$x_{means}$ on delta-dry-matter was found to be 0.4510, $s_2$ to be 1.4837 and n=16, and thus an estimate for t can be calculated as:

$$t_0 = 0.4510/(1.4837/16)_{1/2} = 1.4811$$

which shows that the hypothesis that there is no differences between the dry matter losses of FPC and FPCC can be rejected with more than 90% probability.

Speculatively, the difference in dry matter of 0.4510 g could give cause to a cheese of 1 g or a cheese yield increase of 0.16% or 1.6%.

In summary, the sixteen paired laboratory cheese trials, each using ChyMax™ (FPC) and fermented produced camel chymosin (FPCC) were compared and it was found with more than 90% probability that fermented produced camel chymosin gives lower dry matter loss to whey, reflecting an expectation of a higher cheese yield.

REFERENCES

Dunn-Coleman, N. S., Bloebaum, P., Berka, R. M., Bodie, E., Robinson, N., Armstrong, G., Ward, M., Przetak, M., Carter, G. L., LaCost, R., Wilson, L. J., Kodoma, K. H., Baliu, E. F., Houen, G., Madsen, M. T, Harlow, K. W., Elagamy, E. I. (2000) Physicochemical, molecular and immunological characterization of camel calf rennet: A comparison with buffalo rennet, J. Dairy Res. 67:73-81.

Foltmann, B., Pedersen, V. B., Jacobsen, H., Kauffman, D. and Wybrandt, G. (1977) The complete amino acid sequence of prochymosin. Proc. Natl. Acad. Sci. 74:2321-2324.

Houen, G., Madsen, M. T., Harlow, K. W., Lønblad, P. and Foltman, b. (1996) The primary structure and enzymatic properties of porcine prochymosin and chymosin. Int. J. Biochem. Cell. Biol. 28:667-675.

Kappeler, S. (1998) Compositional and Structural Analysis of Camel Milk Proteins with Emphasis on Protective Proteins, Dissertation ETH No. 12947, Swiss Federal Institute of Technology.

Sambrook, J., Fritsch, E. F. and Maniatis, T. (1989) Molecular cloning. A laboratory manual. $2^{nd}$ edition. Cold Spring Harbor Laboratory Press.

Wangoh, J., Farah, Z. and Puhan, Z. (1993). Extraction of camel rennet and its comparison with calf rennet extract, Milchwissenschaft 48:322-325.

Ward, M., Wilson, L. J., Kodoma, K. H., Rey, M. W. and Berka, R. M. (1990) Improved production of chymosin in Aspergillus by expression of glycoamylase-chymosin fusion, Bio/Technology 8:435-440.

Ward, M., Wilson, L. J. and Kodoma, K. H. (1993) Use of Aspergillus overproducing mutants, cured for integrated plasmid, to overproduce heterologous proteins, Appl. Microbiol. Biotechnol. 39:738-743.

WO 94/16086, Chr. Hansen A/S and Bioteknologisk Institut, 21 Jul. 1994

The invention claimed is:

1. An isolated or non-naturally occurring DNA construct, the nucleic acid sequence of which comprises (I) a coding sequence encoding an expressible protein which is (a) a pre-prochymosin, prochymosin, or chymosin of a mammal of the suborder Tylopoda or (b) a fusion protein comprising a core protein, wherein said fusion protein is cleavable to release said core protein and wherein said core protein is a pre-prochymosin, prochymosin or chymosin of a mammal of the suborder Tylopoda; and (II) appropriate expression signals, operably linked to said coding sequence, permitting the protein to be expressed in a host cell.

2. The DNA construct of claim 1 in which the mammal is of the genus *Camelus*.

3. The DNA construct of claim 1 in which the mammal is *Camelus dromedaries*.

4. An isolated host cell transformed with the DNA construct of claim 1, said cell being one in which said expression signals are operable.

5. A method of producing a Tylopoda protein of interest selected from the group consisting of pre-prochymosin, prochymosin, and chymosin which comprises providing a host cell according to claim 4, cultivating said host cell under conditions where said expressible protein is expressed, if said expressible protein is a fusion protein, cleaving it to release said protein of interest, and harvesting the protein of interest.

6. The method of claim 5 wherein the pre-prochymosin, prochymosin or chymosin is a *Camelus dromedaries* protein.

7. The method of claim 5 wherein the nucleic acid sequence encodes for a fusion protein comprising pre-prochymosin, prochymosin or chymosin.

8. The method of claim 7 wherein the fusion protein comprises glucoamylase or a fragment thereof.

9. The method of claim 5 wherein the pre-prochymosin, prochymosin, chymosin, or fusion protein is secreted.

10. The method of claim 5 wherein the DNA construct comprises pGAMpR.

11. The method of claim 5 wherein the DNA construct is pGAMpR-C as contained in the *Aspergillus niger* var. *awamori* strains deposited under the accession numbers CBS 108915 and CBS 108916.

12. The method of claim 5 wherein the transformed host cell is selected from the group consisting of a bacterial cell, a fungal cell, a yeast cell, a mammalian cell, an insect cell and a plant cell.

13. The method of claim 12 wherein the host cell is *Aspergillus niger* var. *awamori*.

14. The method of claim 13 wherein the *Aspergillus niger* var. *awamori* host cell is selected from the group consisting of CBS 108915 and CBS 108916.

15. The method of claim 5 wherein the yield of pre-prochymosin, prochymosin or chymosin milk clotting activity is at least 25% higher than the yield of bovine pre-prochymosin, bovine prochymosin or bovine chymosin milk clotting activity obtained when using, under identical production conditions, an expression vector which differs only with respect to its coding sequence.

16. The method of claim 5 comprising, as a further step, that the harvested pre-prochymosin, prochymosin or chymosin is subjected to a deglycosylation treatment.

17. The method of claim 5 wherein the host cell is a cell expressing a deglycosylating enzyme.

18. The method of claim 17 wherein the deglycosylating enzyme is endoH.

19. The method of claim 5 in which the mammal is of the genus *Camelus*.

* * * * *

SEQUENCE LISTING

```
<160> NUMBER OF SEQ ID NOS: 7

<210> SEQ ID NO 1
<211> LENGTH: 34
<212> TYPE: DNA
<213> ORGANISM: Artificial Sequence
<220> FEATURE:
<223> OTHER INFORMATION: Primer for PCR amplification

<400> SEQUENCE: 1
cacgtggcgg agtgggatca ccaggatccc tctg                               34

<210> SEQ ID NO 2
<211> LENGTH: 34
<212> TYPE: DNA
<213> ORGANISM: Artificial Sequence
<220> FEATURE:
<223> OTHER INFORMATION: Primer for PCR amplification

<400> SEQUENCE: 2
tctagaggat cagatggcct tggccagccc cacg                               34

<210> SEQ ID NO 3
<211> LENGTH: 35
<212> TYPE: DNA
<213> ORGANISM: Artificial Sequence
<220> FEATURE:
<223> OTHER INFORMATION: Oligonucleotide primer for oligonucleotide-
      based mutagenesis

<400> SEQUENCE: 3
gcgacggtga ctgacacgtg gcgggcagaa ataac                              35

<210> SEQ ID NO 4
<211> LENGTH: 35
<212> TYPE: DNA
<213> ORGANISM: Artificial Sequence
<220> FEATURE:
<223> OTHER INFORMATION: Oligonucleotide for oligonucleotide-based
      mutagenesis

<400> SEQUENCE: 4
gttatttctg cccgccacgt gtcagtcacc gtcgc                              35

<210> SEQ ID NO 5
<211> LENGTH: 11
<212> TYPE: PRT
<213> ORGANISM: Artificial Sequence
<220> FEATURE:
<223> OTHER INFORMATION: Chymosin hydrolizes the peptide bond between
      nitrophenylalanine and Met.
<220> FEATURE:
<221> NAME/KEY: VARIANT
<222> LOCATION: (8)..(8)
<223> OTHER INFORMATION: Xaa = nitrophenylalanine

<400> SEQUENCE: 5

His Pro His Pro His Leu Ser Xaa Met Ala Ile
 1               5                  10
```

```
<210> SEQ ID NO 6
<211> LENGTH: 11
<212> TYPE: PRT
<213> ORGANISM: Artificial Sequence
<220> FEATURE:
<223> OTHER INFORMATION: Chymosin hydrolizes the peptide bond between
      nitrophenylalanine and Ile.
<220> FEATURE:
<221> NAME/KEY: VARIANT
<222> LOCATION: (8)..(8)
<223> OTHER INFORMATION: Xaa = nitrophenylalanine

<400> SEQUENCE: 6

Arg Pro Arg Pro Arg Pro Ser Xaa Ile Ala Ile
 1               5                  10

<210> SEQ ID NO 7
<211> LENGTH: 4
<212> TYPE: PRT
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: Xaa is Ser or Thr

<400> SEQUENCE: 7

Asp Thr Gly Xaa
 1
```